US011090064B2

(12) United States Patent
Aho et al.

(10) Patent No.: US 11,090,064 B2
(45) Date of Patent: *Aug. 17, 2021

(54) DEVICES AND METHODS FOR VERTEBROSTENTING

(71) Applicant: GLOBUS MEDICAL, INC., Audubon, PA (US)

(72) Inventors: John Martin Aho, Lunenburg, MA (US); Andrew R. Sennett, Hanover, MA (US)

(73) Assignee: Globus Medical Inc., Audubon, PA (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/378,616

(22) Filed: Apr. 9, 2019

(65) Prior Publication Data
US 2019/0231368 A1 Aug. 1, 2019

Related U.S. Application Data

(60) Division of application No. 15/265,875, filed on Sep. 15, 2016, now Pat. No. 10,292,716, which is a continuation of application No. 12/729,724, filed on Mar. 23, 2010, now Pat. No. 9,480,485.

(60) Provisional application No. 61/210,771, filed on Mar. 23, 2009.

(51) Int. Cl.
*A61B 17/16* (2006.01)
*A61B 17/00* (2006.01)

(52) U.S. Cl.
CPC ...... *A61B 17/1642* (2013.01); *A61B 17/1617* (2013.01); *A61B 17/1631* (2013.01); *A61B 17/1671* (2013.01); *A61B 2017/00367* (2013.01)

(58) Field of Classification Search
CPC ............ A61B 17/1613; A61B 17/1615; A61B 17/1617; A61B 17/1631; A61B 17/1642
See application file for complete search history.

(56) References Cited

U.S. PATENT DOCUMENTS

| | | | | |
|---|---|---|---|---|
| 5,448,989 A | * | 9/1995 | Heckele | A61B 1/0055 600/104 |
| 6,575,979 B1 | * | 6/2003 | Cragg | A61B 17/32002 606/86 R |
| 2006/0184188 A1 | * | 8/2006 | Li | A61B 17/1617 606/180 |

* cited by examiner

*Primary Examiner* — Si Ming Ku

(57) ABSTRACT

The invention relates to devices and methods for creating a curvilinear cavity within a vertebral body or other body structure. An example method of forming a void in bony structure includes accessing a bony structure with a cannula, inserting a distal end of a combined drill and reaming device through the cannula and into the bony structure, manipulating the distal end of the combined drill and reaming device to create a void in the bony structure, and removing the distal end of the combined drill and reaming device from the cannula.

9 Claims, 36 Drawing Sheets

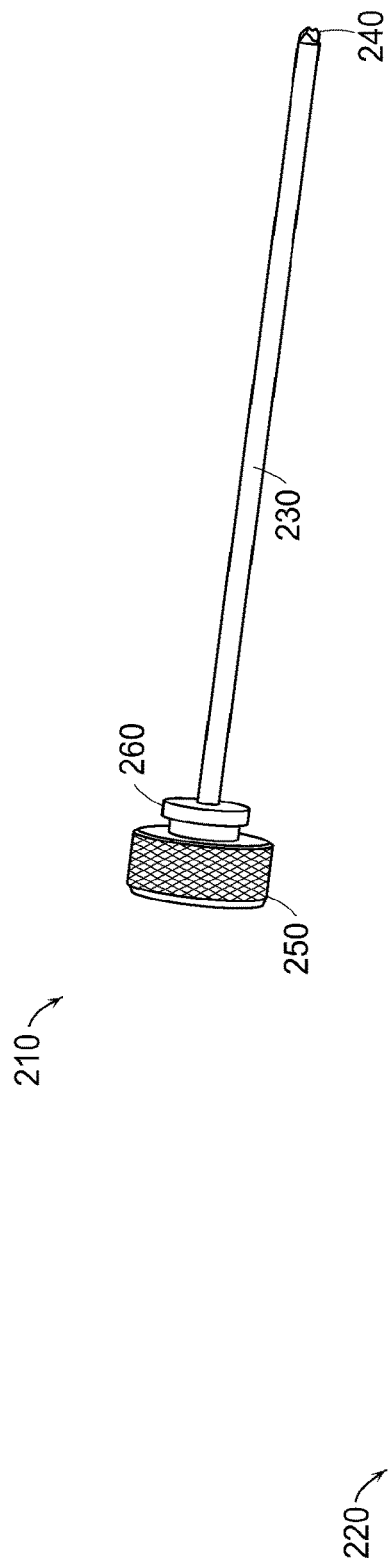
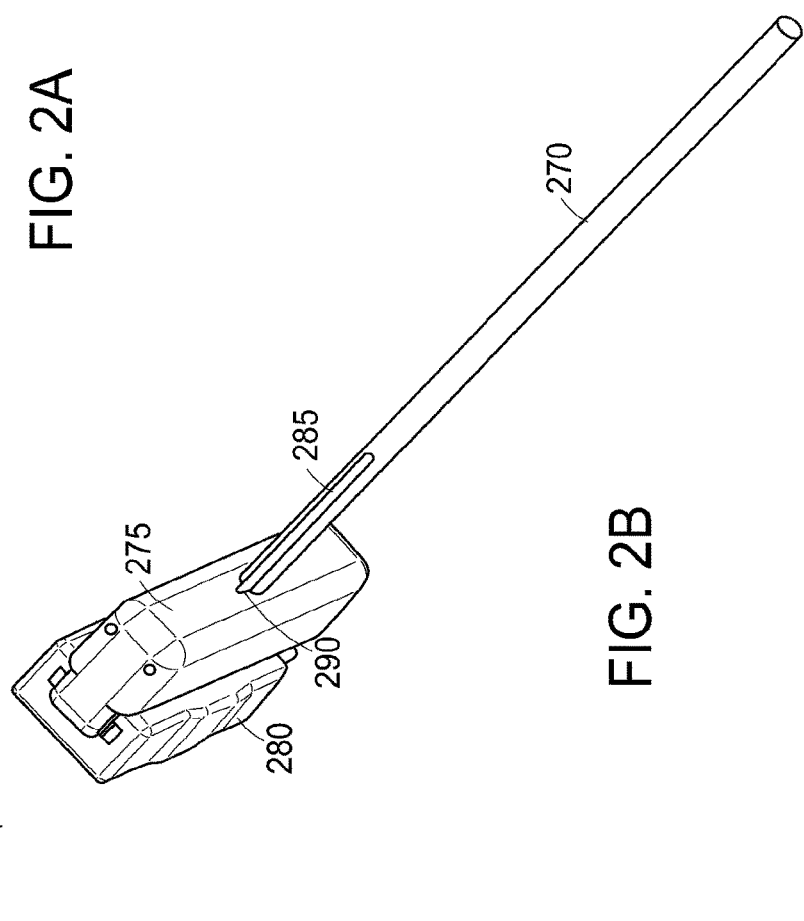
FIG. 2A
FIG. 2B

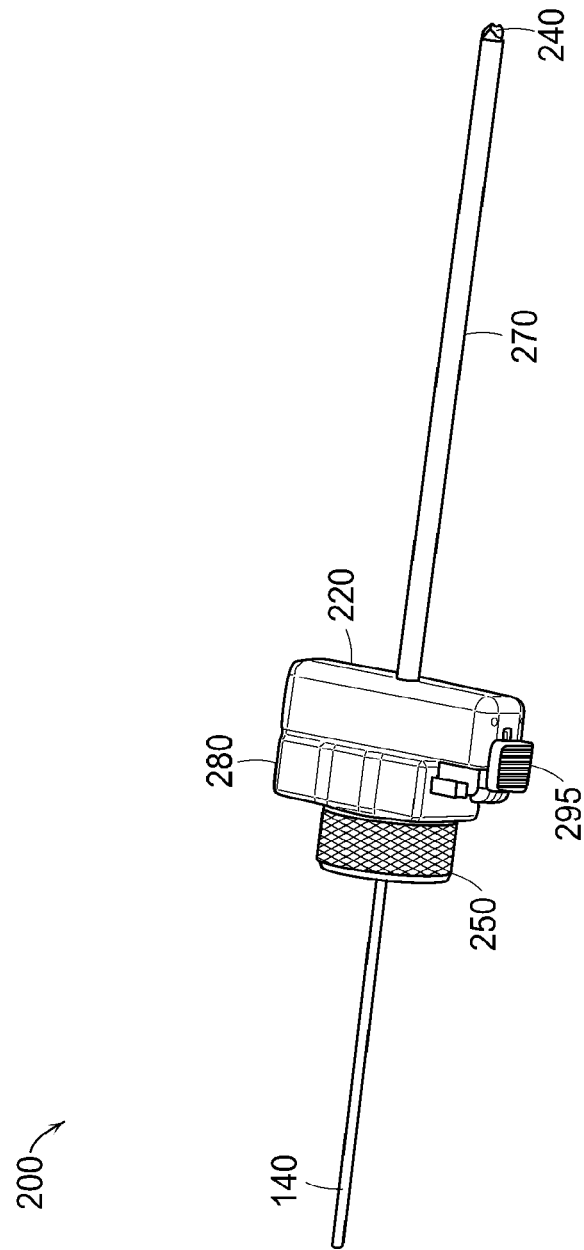

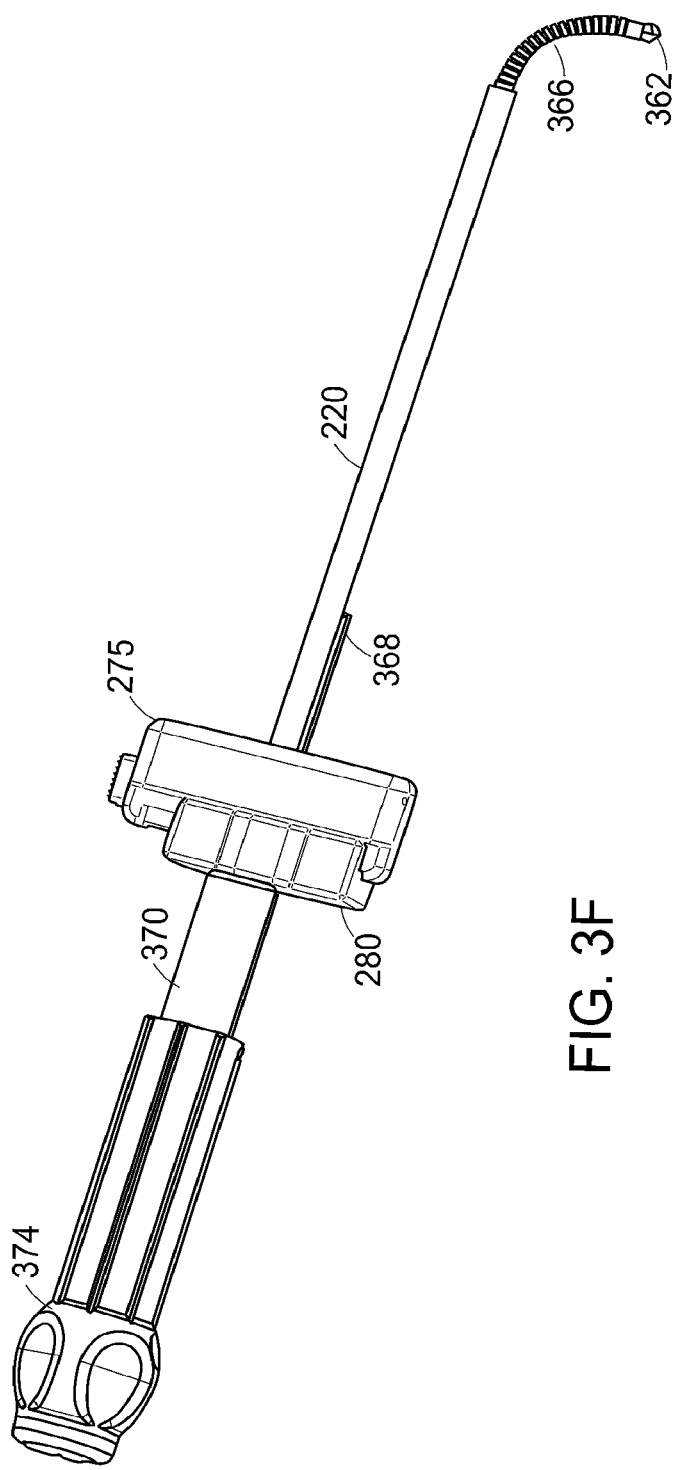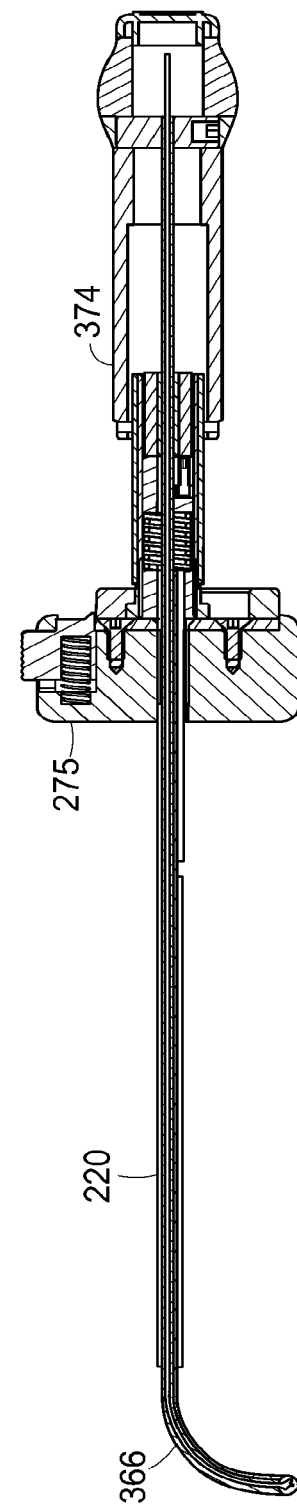
FIG. 3F
FIG. 3G

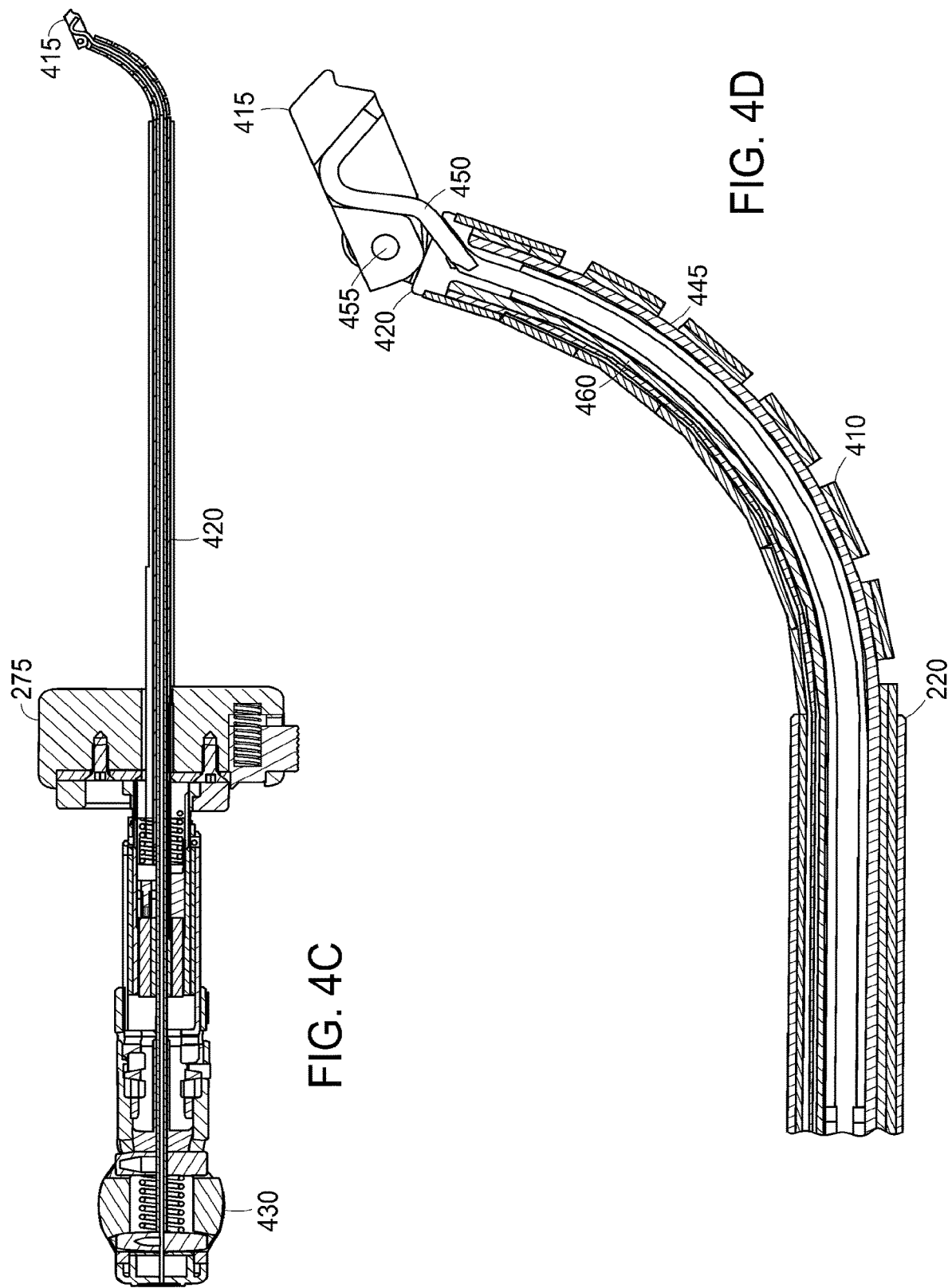

DEVICES AND METHODS FOR VERTEBROSTENTING

CROSS-REFERENCE TO RELATED APPLICATIONS

This application is a divisional application of U.S. patent application Ser. No. 15/265,875 filed on Sep. 15, 2016, which is a continuation application of U.S. patent application Ser. No. 12/729,724, filed Mar. 23, 2010 which is related to U.S. patent application Ser. No. 11/957,022, filed Dec. 14, 2007, U.S. patent application Ser. No. 11/957,039, filed Dec. 14, 2007, U.S. patent application Ser. No. 12/486,439, filed Jun. 17, 2009, U.S. provisional patent application Ser. No. 60/875,114 filed Dec. 15, 2006, U.S. provisional patent application Ser. No. 60/875,173 filed Dec. 15, 2006, and U.S. provisional patent application Ser. No. 61/073,184 filed Jun. 17, 2008, the disclosures of all of which are being incorporated herein by reference in their entirety. U.S. patent application Ser. No. 12/729,724 claims priority to and the benefit of U.S. provisional patent application Ser. No. 61/210,771 filed Mar. 23, 2009, the disclosure of which is being incorporated herein by reference in its entirety.

FIELD OF THE INVENTION

The present invention relates generally to the field of orthopedic devices, and more particularly to a systems and methods that can be used to create cavities in vertebral bodies to facilitate bone cement treatment of a vertebral compression fracture.

BACKGROUND OF THE INVENTION

There are many disease states that cause bone defects in the spinal column. For instance, osteoporosis and other metabolic bone conditions weaken the bone structure and predispose the bone to fracture. If not treated, certain fractures and bone defects of the vertebral body may produce intolerable pain, and may lead to the development of deformity and severe medical complications.

Bone weakening may also result from benign or malignant lesions of the spinal column. Tumors often compromise the structural integrity of the bone and thus require surgical stabilization and repair of defects with biocompatible materials such as bone grafts or cements. Bone tumors of the spine are relatively common, and many cause vertebral compression fracture.

More than 700,000 osteoporotic compression fractures of the vertebrae occur each year in the United States—primarily in the elderly female population. Until recently, treatment of such fractures was limited to conservative, non-operative therapies such as bed rest, bracing, and medications.

One surgical technique for treating vertebral compression fracture can include injecting or filling the fracture bone or bone defect with biocompatible bone cement. A relatively new procedure known as "vertebroplasty" was developed in the mid 1980's to address the inadequacy of conservative treatment for vertebral body fracture. This procedure involves injecting radio-opaque bone cement directly into a fracture void, through a minimally invasive cannula or needle, under fluoroscopic control. The cement is pressurized by a syringe or similar plunger mechanism, thus causing the cement to fill the void and penetrate the interstices of a broken trabecular bone. Once cured, the cement stabilizes the fracture and eliminates or reduces pain. Bone cements are generally formulations of non-resorbable biocompatible polymers such as PMMA (polymethylmethacrylate), or resorbable calcium phosphate cements which allow for the gradual replacement of the cement with living bone. Both types of bone cements have been used successfully in the treatment of bone defects secondary to compression fractures of the vertebral body.

One clinical issue associated with vertebroplasty is containment of the cement within the margins of the defect. For instance, an osteoporotic compression fracture usually compromises portions of the cortical bone creating pathways to cement leakage. Thus, there is a risk of cement flowing beyond the confines of the bone into the body cavity. Cement leakage into the spinal canal, for instance, can have grave consequences to the patient.

Yet another significant risk associated with vertebroplasty is the injection of cement directly into the venous system, since the veins within the vertebral body are larger than the tip of the needle used to inject the cement. A combination of injection pressure and inherent vascular pressure may cause unintended uptake of cement into the pulmonary vessel system, with potentially disastrous consequences including embolism to the lungs.

One technique which has gained popularity in recent years is a modified vertebroplasty technique in which a "balloon tamp" is inserted into the vertebral body via a cannula approach to expand or distract the fractured bone and create a void within the cancellous structure. Balloon tamps are inflated using pressurized fluid such as saline solution. The inflation of a balloon membrane produces radial forces on the surface of the membrane and forms a cavity in the bone. When deflated and removed, the membrane leaves a cavity that is subsequently filled with bone cement. The formation of a cavity within the bone allows for the injection of more viscous cement material, which may be relatively less prone to leakage.

In certain instances, such as the treatment of acute or mobile fractures, the balloon is also effective at "reducing" the fracture and restoring anatomic shape to a fractured body. In particular, balloon dilatation in bone is maximally effective if the balloon device is targeted inferior to, or below, the fracture plane. In this instance, the balloon dilatation may distract, or lift, a fracture bone fragment, such as the vertebral body endplate.

In other instances, such as chronic or partially healed fractures, balloons are less effective at "reducing" the fracture because radial forces are insufficient. Often the bone in an incompletely healing fracture is too dense and strong, and requires more aggressive cutting treatment, such as a drill or reamer tool to create a sufficient cavity. In these more challenging cases, the ability to inject bone cement into a cavity created by a balloon or a reamer in the vicinity of the fracture is typically sufficient to stabilize the bone and relieve pain, even in the absence of fracture reduction.

One limitation to the use of such methods has been the difficulty in targeting the location at which the cavity should be created. Known techniques require access to the vertebral body using straight cutting and reaming tools which are only able to access a limited region of the vertebral body being treated, generally only within one side of the vertebral body. A cavity created using these techniques can only treat one side of a vertebral body being targeted, resulting in an uneven distribution of bone cement that cannot completely stabilize the vertebral body. As a result, multiple entry points on different sides of the vertebral body are generally required in order to provide a symmetrical distribution of bone cement around a central axis of the vertebral body. These multiple entry points significantly increase the time necessary for the procedure, the portion of the body being treated, and the amount of bone cement being injected, and, as such, can significantly increase the risks associated with treatment of a patient, as well as costs.

SUMMARY OF THE INVENTION

The present invention is directed towards novel methods and devices for preparing a cavity in bone. The methods and devices disclosed herein can allow a cavity to be created in a vertebral body along a curvilinear pathway, allowing for a substantially symmetrical distribution of bone cement over a central vertical axis of a vertebral body. This can allow a vertebral body to be successfully and completely stabilized from a single surgical access point and using a single stent device.

One aspect of the invention relates to a method of forming a void in bony structure, the method including the steps of accessing a bony structure with a cannula, inserting a distal end of a combined drill and reaming device through the cannula and into the bony structure, manipulating the distal end of the combined drill and reaming device to create a void in the bony structure, and removing the distal end of the combined drill and reaming device from the cannula. The void formed may be a curvilinear void.

In one embodiment, the combined drill and reaming device includes a pivotable blade at a distal end thereof. The step of manipulating of the distal end of the combined drill and reaming device may include a simultaneous rotation and curvilinear translation of the pivotable blade. The step of manipulating of the distal end of the combined drill and reaming device may include a simultaneous rotation and curvilinear translation of the pivotable blade away from a proximal end of the combined drill and reaming device while in a non-deployed configuration to drill a curvilinear void having a first effective cross-sectional diameter. The step of manipulating of the distal end of the combined drill and reaming device may further include pivoting the pivotable blade to a deployed configuration and a simultaneous rotation and curvilinear translation of the deployed pivotable blade towards a proximal end of the combined drill and reaming device to ream a curvilinear void having a second enlarged effective cross-sectional diameter.

In one embodiment, the cannula is substantially straight. The combined drill and reaming device may include a flexible drill shaft assembly. In one embodiment, the step of manipulating the distal end of the combined drill and reaming device includes inducing a curvature in the distal end of the flexible drill shaft assembly. The flexible drill shaft assembly may include a lever and cam sub assembly for varying a force used to apply the curvature to the distal end of the flexible drill shaft assembly. The method may include manipulating at least one lever to a first position to reduce the force on the distal end of the flexible drill shaft assembly prior to inserting the distal end of the drill device through the cannula and releasing the at least one lever to a second position to increase the force on the distal end of the flexible drill shaft assembly after inserting the distal end of the drill device through the cannula. The distal end of the flexible drill shaft assembly may have a predetermined curvature when the at least one lever is in a released configuration. The method may include moving the lever to the first position to reduce the force on the distal end of the flexible drill shaft assembly prior to removing the distal end of the drill and reaming device from the cannula.

In one embodiment, the flexible drill shaft assembly includes a pivotable blade, a flexible rotatable drive shaft coupled to the pivotable blade, and a flexible, moveable and non-rotatable housing. The combined drill and reaming device may include a locking means. In one embodiment, the method includes locking the combined drill and reaming device into the cannula using the locking means prior to forming the void, and unlocking the combined drill and reaming device from the cannula after forming the void and prior to removing the distal end of the drill and reaming device. In one embodiment, the combined drill and reaming device is manipulated in response to a rotation of an element at a proximal end of the drill and reaming device.

Another aspect of the invention includes an apparatus for forming a void in bony structure including a handle and a flexible drill shaft assembly extending from a distal end of the handle. The flexible drill shaft assembly includes a pivotable blade located at a distal end of the flexible drill shaft assembly, wherein the pivotable blade is configured to cut in both a non-deployed and deployed position, a flexible rotatable drive shaft coupled to the pivotable blade, and a flexible, moveable and non-rotatable housing. The apparatus may be adapted to form a curvilinear void.

In one embodiment, the pivotable blade is adapted to form the curvilinear void by simultaneous rotation and curvilinear translation of the pivotable blade away from a proximal end of the apparatus while in a non-deployed configuration to drill a curvilinear void having a first effective cross-sectional diameter. The pivotable blade may be adapted to pivot from a first non-deployed position to a second deployed position. In one embodiment, the apparatus includes means for deploying the pivotable blade. The pivotable blade may be adapted to form the curvilinear void by simultaneous rotation and curvilinear translation of a deployed pivotable blade towards a proximal end of the combined drill and reaming device to ream a curvilinear void having a second enlarged effective cross-sectional diameter.

In one embodiment, the flexible drill shaft assembly is adapted to form a curvature at a distal end thereof. The apparatus may include at least one lever and cam sub assembly for varying a force used to apply the curvature. The at least one lever may have a first position at which the force is less than at a second position of the lever.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2A is schematic perspective view of a trocar, used in accordance with one embodiment of the invention;

FIG. 2B is schematic perspective view of a cannula, in accordance with one embodiment of the invention;

FIG. 2D is a schematic perspective view of a trocar inserted with the cannula of FIG. 2B, in accordance with one embodiment of the invention;

FIG. 3F is a schematic perspective view of the drill assembly of FIG. 3E inserted within a cannula, in accordance with one embodiment of the invention;

FIG. 3G is a sectional side view of the drill assembly of FIG. 3E inserted within a cannula;

FIG. 4C is a sectional side view of the reamer assembly of FIG. 4A inserted within a cannula;

FIG. 4D is an enlarged sectional side view of the distal end of the reamer assembly of FIG. 4A;

DETAILED DESCRIPTION OF THE PREFERRED EMBODIMENTS

To maximize the effectiveness of balloon dilatation or bone cutting with a reamer, it would be beneficial to more effectively target the location within the bone prior to dilatation of the balloon. In the specific case of vertebral body fracture, there are anatomical challenges to targeting with minimally invasive instrumentation. Safe passage of instruments and balloon catheters from the posterior surgical approach is generally achieved through a straight cannula positioned within the pedicle of the vertebral body, or just lateral to the pedicle to avoid potentially dangerous penetration of the cannula in the spinal canal. This anatomically defined trajectory often does not align with, or target, the fracture within the vertebral body. Therefore, there are limitations in current techniques to effectively target the fracture.

There are numerous devices disclosed in the art to make the injection of cement into the vertebral body a safer procedure. One novel device, an implantable cement-directing stent device, is disclosed in U.S. Patent Publication No. 2005/0261781 A1 to Sennett et al., the disclosure of which is incorporated herein by reference in its entirety. The implantable cement-directing stent device provides a means to temporarily stabilize a fractured vertebral body after cavity creation during cement injection, while also directing the flow of cement anteriorly within the vertebral body to prevent unwanted cement flow near the spinal canal. This disclosure presents additional novel devices and methods of use to fully describe the technique of "vertebrostenting" to treat vertebral compression fracture using conventional stent devices or the improved stent device of Sennett et al.

Needle

In one embodiment of the invention, access to the vertebral body can be achieved using a pointed needle or wire to pierce the skin and underlying tissue and entering into the pedicle, a depression of the vertebral body, until the needle is held fast. The needle can then be pressed into the vertebral body until it is held firmly in place by the wall of the vertebral body. The needle can then become a guide for the placement of subsequent devices.

Figure 1A:
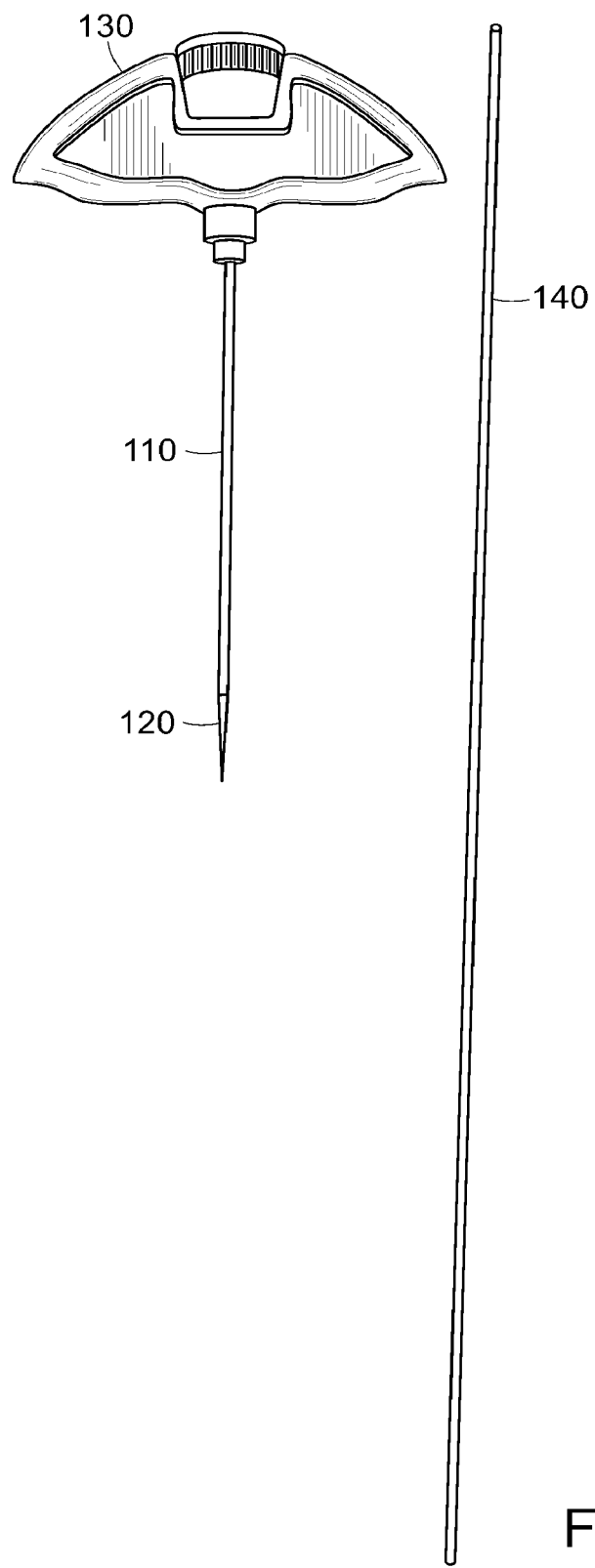
FIG. 1A is a schematic plan view of a Jamshidi needle and K-wire, used in accordance with one embodiment of the invention.

In an example embodiment of the invention, a Jamshidi needle and K-wire arrangement can be used to provide a guide for placement of subsequent devices into the vertebral body. A Jamshidi Needle is a long, tapered combination needle and drill that can be used for insertion into bone. An example Jamshidi needle and K-wire can be seen in FIG. 1A. Here, the Jamshidi needle 110 can include a tapered distal end 120 and a handle 130 at its proximal end. The elongate Jamshidi needle 110 can be hollow, to allow insertion of the K-wire 140 through the needle 140.

Figure 1B:
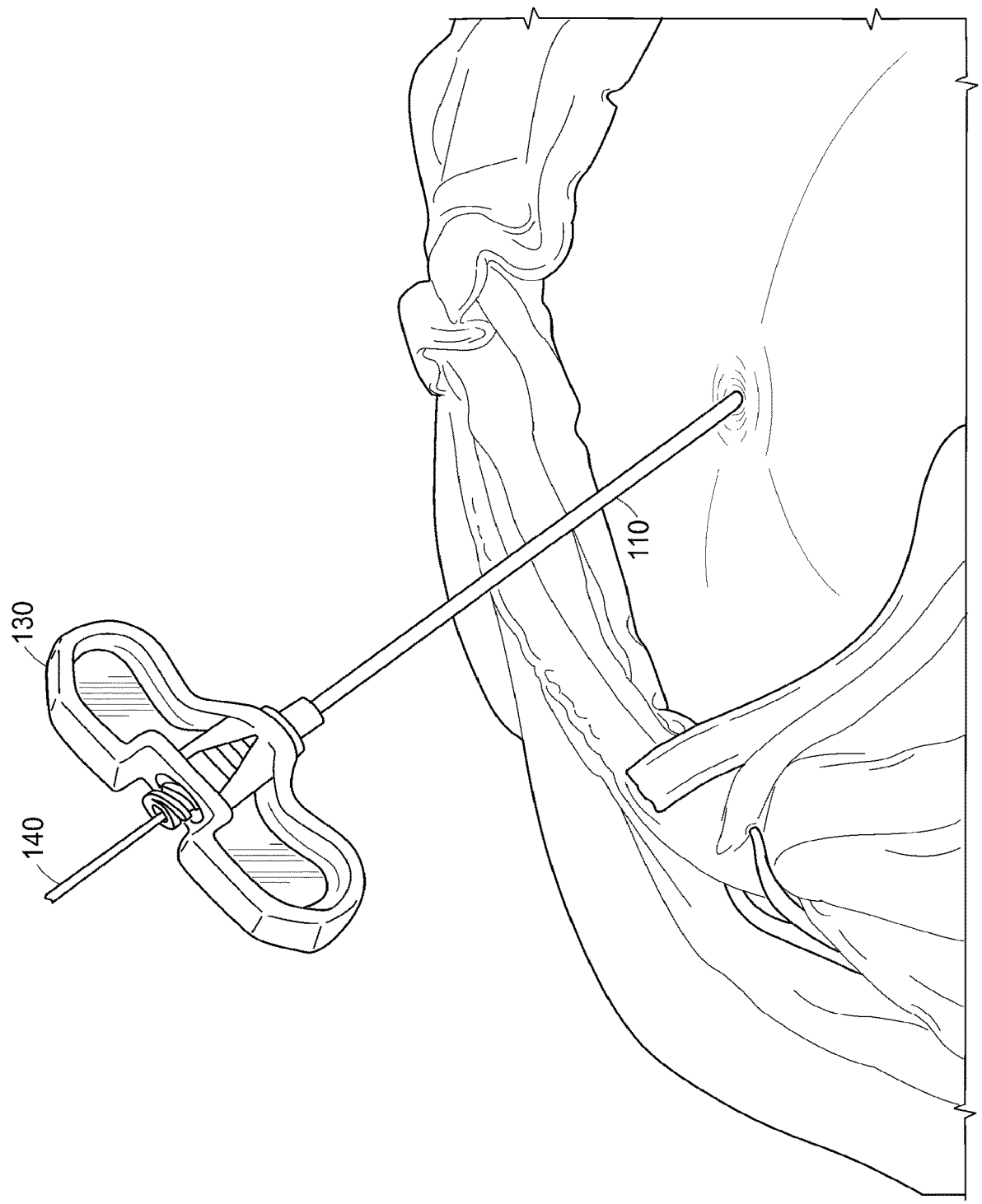
FIG. 1B is a picture of a Jamshidi needle being inserted into a patient, in accordance with one embodiment of the invention.

In operation, the tapered distal end 120 is inserted through the skin and underlying tissue and pressed against the outer wall of the vertebral body. The K-wire 140 can then be inserted through the hollow elongate needle 110 such that the distal end of the K-wire is forced against the wall of the vertebral body. The Jamshidi needle 110 and K-wire 140 can be forced into the wall of the vertebral body to any depth appropriate for the procedure. The Jamshidi needle 110 can then be removed, leaving the K-wire 140 in place to act as a guide needle for the placement of subsequent devices. An example of a Jamshidi needle 110 and K-wire 140 inserted through the skin and underlying tissue of a patient can be seen in FIG. 1B. In alternative embodiments, any appropriate needle type or other device may be used to provide initial access to the vertebral body.

Cannula & Trocar

In one embodiment of the invention, access to the vertebral body can be achieved through the use of a trocar and cannula assembly. This trocar and cannula assembly can be inserted over an already inserted guide wire or needle, such as the K-wire described above, or be inserted directly without the need for a guide wire.

Figure 2C:
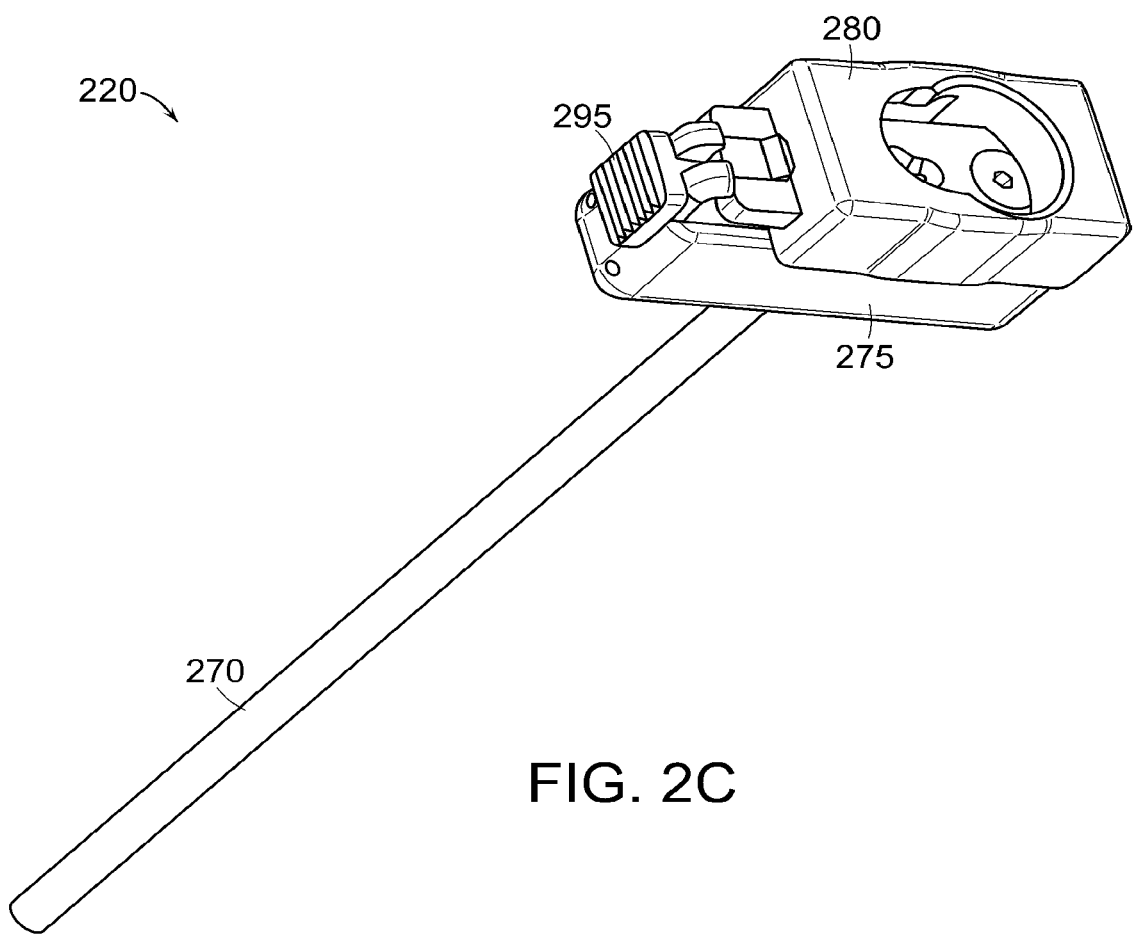
FIG. 2C is another schematic perspective view of the cannula of FIG. 2B.

One embodiment of a trocar and cannula assembly is shown in FIGS. 2A-2F. In this embodiment, the trocar and cannula assembly 200 can include a trocar 210 and a cannula 220. An example trocar 210 is shown in FIG. 2A. In this embodiment, the trocar 210 includes a hollow shaft 230 with a sharpened tip 240, and an impact handle 250 or knob coupled to the hollow shaft 230. The impact handle 250 also has a cylindrical locking flange 260, for releasable interlocking with the cannula 220. The trocar 210 can be configured to fit over a guide wire or needle.

An example cannula 220 is shown in FIGS. 2B and 2C. The hollow cannula 220 can include a thin walled straight tube 270 and a handle 275 with a locking feature 280 attached to the hollow tube 270. The locking feature can include a button, slide, latch, or other appropriate mechanism for releasable engagement with a flange. In the embodiment of FIGS. 2B and 2C, the locking feature 280 includes a locking slide 280 and a locking slide latch 295, wherein the locking slide latch 295 is configured to engage with the locking slide 280 and releasably hold the locking slide 280 in either a closed or open position. The thin walled tube 270 can also have a slot 285 along its axis on the proximal side that is continuous with a slot 290 in the handle 275. The tube slot 285 and the handle slot 290 can be used for instrument orientation or drills, reamers, etc. disposed in the cannula 220.

The handle 275 may be coupled to the thin walled straight tube 270 of the cannula 220 by any appropriate means, including, but not limited to, bonding, pressure fitting, threading, or any combination thereof. The handle 275 may be a plastic, metal, or any other suitable material. The handle 275 can include a locking feature for releasable retention of an instrument placed within the cannula 220. In one embodiment, the handle 275 can include a number of holes through its length, fitted with stainless steel rods, that may be used by the surgeon, under fluoroscopy, for circumferential orientation of the handle 275 and the cannula 220 to ensure the desired relationship between the cannula 220 and the vertebral body.

In one embodiment, the trocar 210 fits within the thin walled straight tube 270 of the cannula 220, and releasably locks to the locking feature 280 of the cannula 220 via the locking flange 260. When locked together, the sharp tip 240 of the trocar 210 can protrude beyond the end of the thin walled straight tube 270 of the cannula 220. In an alternative embodiment, the cannula may include a flexible hollow tube, or a curved hollow tube, allowing the cannula to be placed over a curved guide wire or other curved object.

In use, the trocar 210 and the cannula 220 may be deployed over a guide needle or wire and pressed into the vertebral body, with the trocar 210 providing the displacement and/or cutting means needed to force the cannula through the skin and underlying tissue of a patient and up against, and possibly through, the wall of a vertebral body. The guide wire may be a K-wire 140 as described above, or be any other appropriate needle, piercer, or guiding wire element. Once the cannula 220 is inserted through the outer wall of the vertebral body, the trocar 210 and guide needle can be removed, leaving the hollow cannula 220 in place as an access passageway for subsequent instruments and tools.

An example of a trocar 210 and guide wire 140 inserted through a cannula 220 can be seen in FIG. 2D. In FIG. 2D, the impact handle 250 of the trocar 210 is releasably coupled to the handle 275 of the cannula 220 by the locking feature 280. In one embodiment, the trocar tip 240 can protrude beyond the end of the thin walled straight tube 270 of the cannula 220 and can be rotated relative to the cannula tube 270, if desired. The entire trocar 210 and cannula 220 assembly is placed over the guidewire 140, that was previously inserted into the vertebral body. In one embodiment, a small mallet can be used to tap the trocar 210 to enlarge the hole until the cannula 220 is pressed into the vertebral body to a desired depth. The trocar 210 can then be unlatched from the handle 275 and withdrawn. At this point, the needle or guidewire 295 can also removed, leaving the cannula 220 in place and held immovably by the wall of the vertebral body.

Figure 2E:
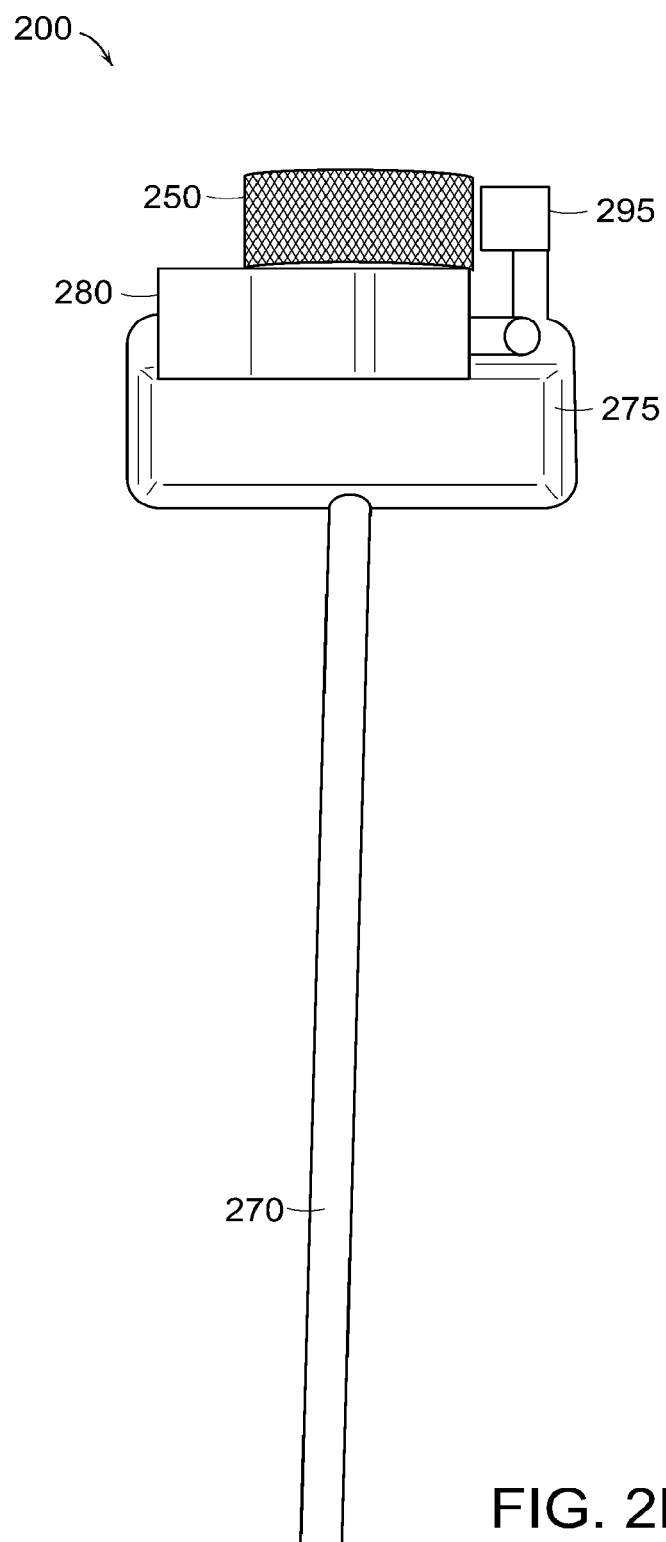
FIG. 2E is a schematic plan view of a cannula, in accordance with one embodiment of the invention.
Figure 2F:
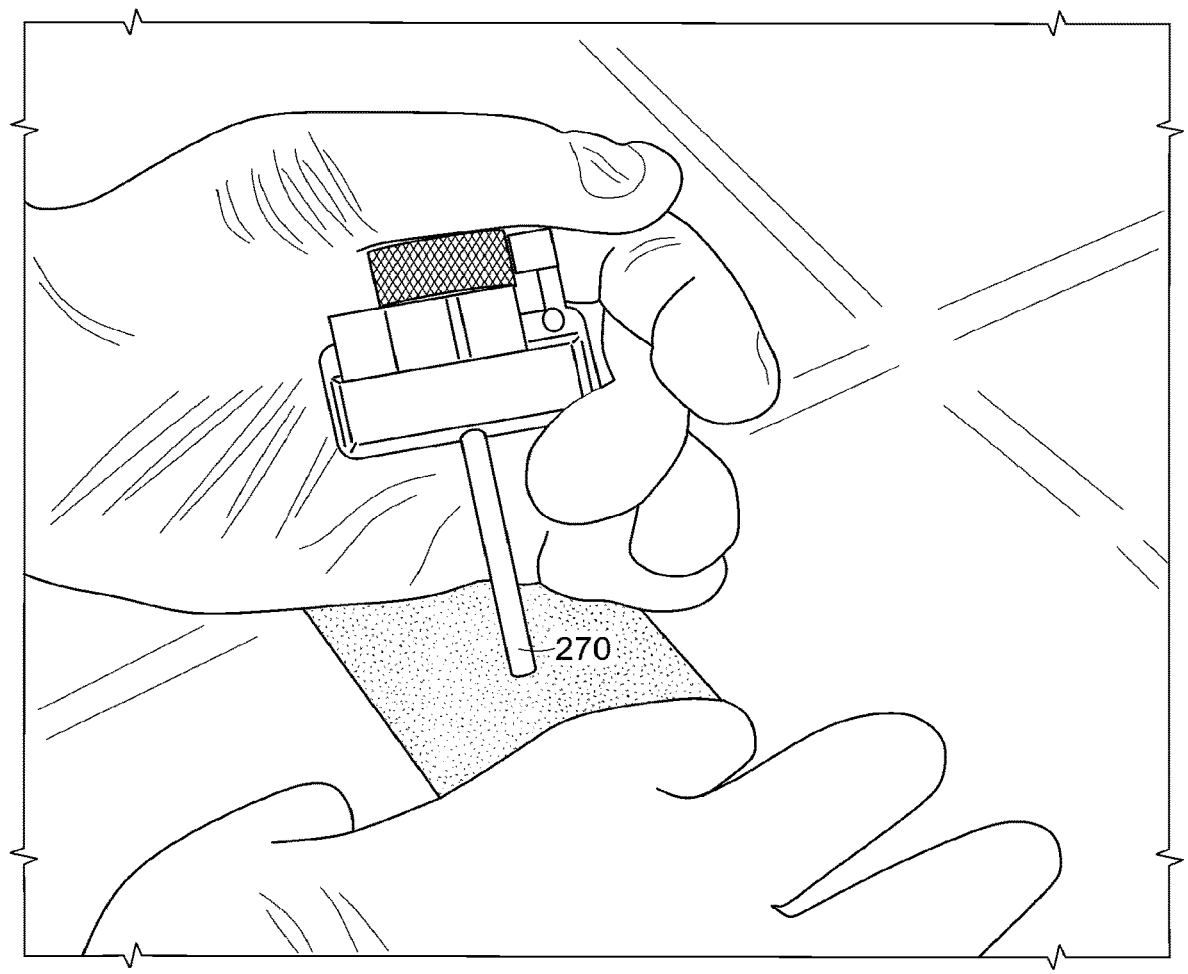
FIG. 2F is a picture of a trocar and cannula being inserted into a patient, in accordance with one embodiment of the invention.

An example embodiment of a cannula 220 and handle 275 can be seen in FIG. 2E. An example of this cannula 220 inserted into a patient can be seen in FIG. 2F.

Drill

In one embodiment of the invention, once the cannula is in place, the next step is to drill a curved hole in the vertebral body. The curved hole may be needed to make a cavity in the vertebral body that will go across the interior of the vertebral body so that medical cement will fill and support the entire vertebral body without the need to drill from both sides. One embodiment of the invention can include a means of providing a drilled curved path in the vertebral body through the use of a curved drilling device. Example curved drilling devices are shown in FIGS. 3A-3I.

Figure 3A:
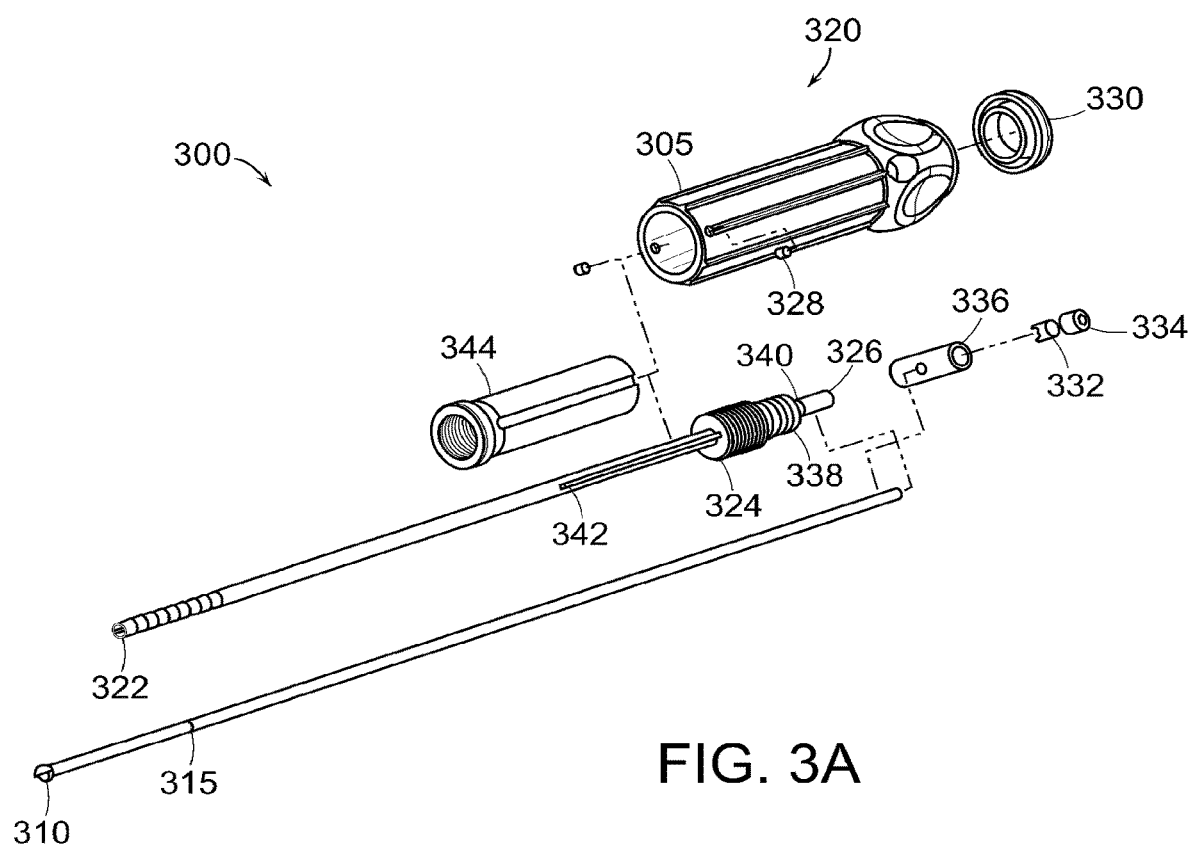
FIG. 3A is an exploded schematic perspective view of a drill assembly, in accordance with one embodiment of the invention.
Figure 3B:
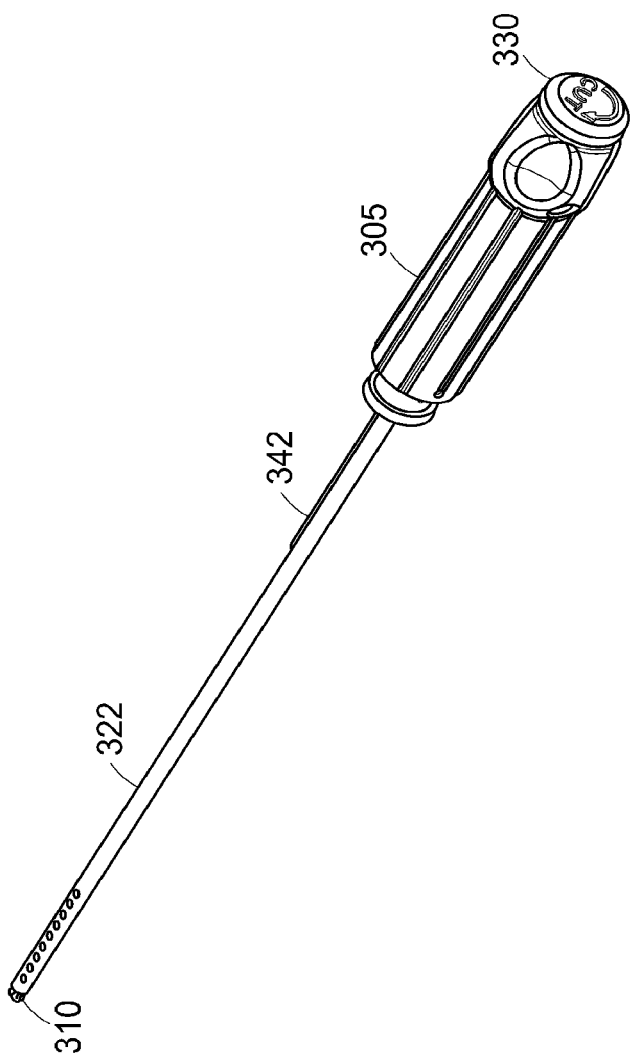
FIG. 3B is a schematic perspective view of the drill assembly of FIG. 3A.
Figure 3D:
FIG. 3D is a schematic end view of the drill assembly of FIG. 3A.
Figure 3C:
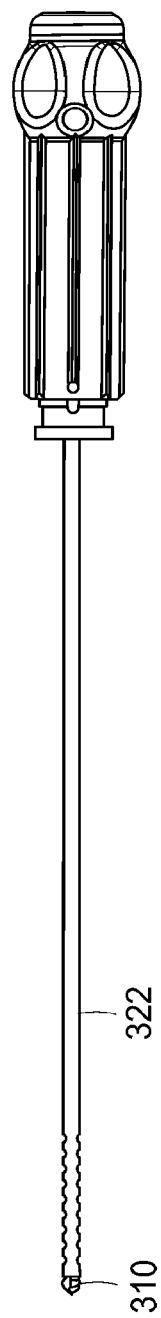
FIG. 3C is a schematic side view of the drill assembly of FIG. 3A.

In one embodiment of the invention, as shown in FIGS. 3A and 3B, the curved drill device 300 can include a drive handle 305, a sharp tip 310 attached to a flexible torque transmitting drive shaft 315, and a handle drive assembly 320. The flexible drive shaft 315 can be secured and contained by a spring loaded, flexible, slotted metal tube 322 having a feedscrew assembly 324 attached therewith. The proximal end of the drive shaft 315 can include a solid tube 326 bonded, or otherwise coupled, to the flexible shaft 315 component and having sufficient torque transmission capability to drive the shaft assembly. The rotating shaft/sharp tip 310 assembly can further be coupled to the handle assembly 320 by a cross pin 328, or other appropriate device, which can engage with a nut 344 located within the handle 305 and threaded onto the feedscrew assembly 324.

The handle drive assembly can include a number of components, including, but not limited to, a cap 330 for the handle, a clamp 332 for the torque tube, a locking element 334 for the torque tube, and a retainer element 336 for the torque tube. The retainer element 338 can be coupled to a spring element 340 to provide a spring force to a band or other element configured to provide a force to the distal portion of the flexible drive shaft 315 and slotted metal tube 322 to produce the correct curvature at the distal end of the drill 300.

One embodiment of the invention can include an inner tube sized to slide within the outer slotted tube. This inner tube can have an extensive laser cut opening along its distal portion. When assembled, the reduced cross section of this section of the inner tube lies adjacent to the slotted portion of the outer tube along the inside or concave side of the slotted tube. A compression spring of optimized stiffness can be coupled to the inner tube and the outer slotted tube at the proximal end by a lock washer, or other appropriate mechanism, that can be secured to a slot in the proximal end of the inner tube. When the washer is engaged, a tensile force is induced on the inner tube which causes the outer tube assembly to bend at the distal end. Upon bending, the slots on the medial side, which have been designed with gradually decreasing depth to encourage sequential distal to proximal deflection, can close. Therefore, when fully assembled under load of the spring, the outer slotted metal tube can assume a curved orientation with a desired radius of curvature. Since the slotted metal tube is itself flexible being made from hard temper stainless steel, or other appropriate material, it can be straightened against the force of the spring to pass through a straight cannula.

In one embodiment, the drive handle of the drill 300 can be a two part assembly featuring a grip feature suitable to allow manual rotation, coupled to a rotator component having locking flange. The locking flange can be designed to mate with the locking feature of a cannula handle to prevent axial movement but allow rotation. The rotator component can have a female thread throughout its length which can mate with a feedscrew slotted tube assembly. The feedscrew and a key are welded, or otherwise coupled, to the proximal end of the slotted tube.

When assembled to the hollow cannula, the key component 342 can slideably mate with the hollow cannula axial slot, which can rotationally lock the drill's curved slotted tube 322 in a preferred circumferential orientation. Therefore, when the handle assembly is rotated, the slotted tube advances in a fixed rotational orientation relative to the handle assembly at a pace equal to the thread pitch of the feedscrew. The rotating flexible drive shaft assembly, which is axially constrained within the slotted metal tube 322, also advances with the pitch of the feedscrew. The sharp rotating tip 310, by the combined forces of the feedscrew advance and internal spring force curving the shaft, cuts and advances on a curved helical path when the handle is rotated. Conversely, when the handle is counter rotated, the sharp tip retracts along the same curved helical path. If the lock engaging the curved drill is disassembled from the cannula, the device may be slideably removed from the cannula.

In operation, the distal end of the curved tube 322 of the drill can be slotted, perforated, composed of a different and or thinner material, or otherwise adapted to promote bending of the distal end. Any appropriate material, such as stainless steel, aluminum, or other metal, or a plastic or composite material may be used for the drilling device, as long as the material can provide sufficient strength, flexibility, resiliency, and resistance to fatigue. In one embodiment, different components of the drilling device can be constructed from different materials, including any of the materials described herein.

Figure 3E:
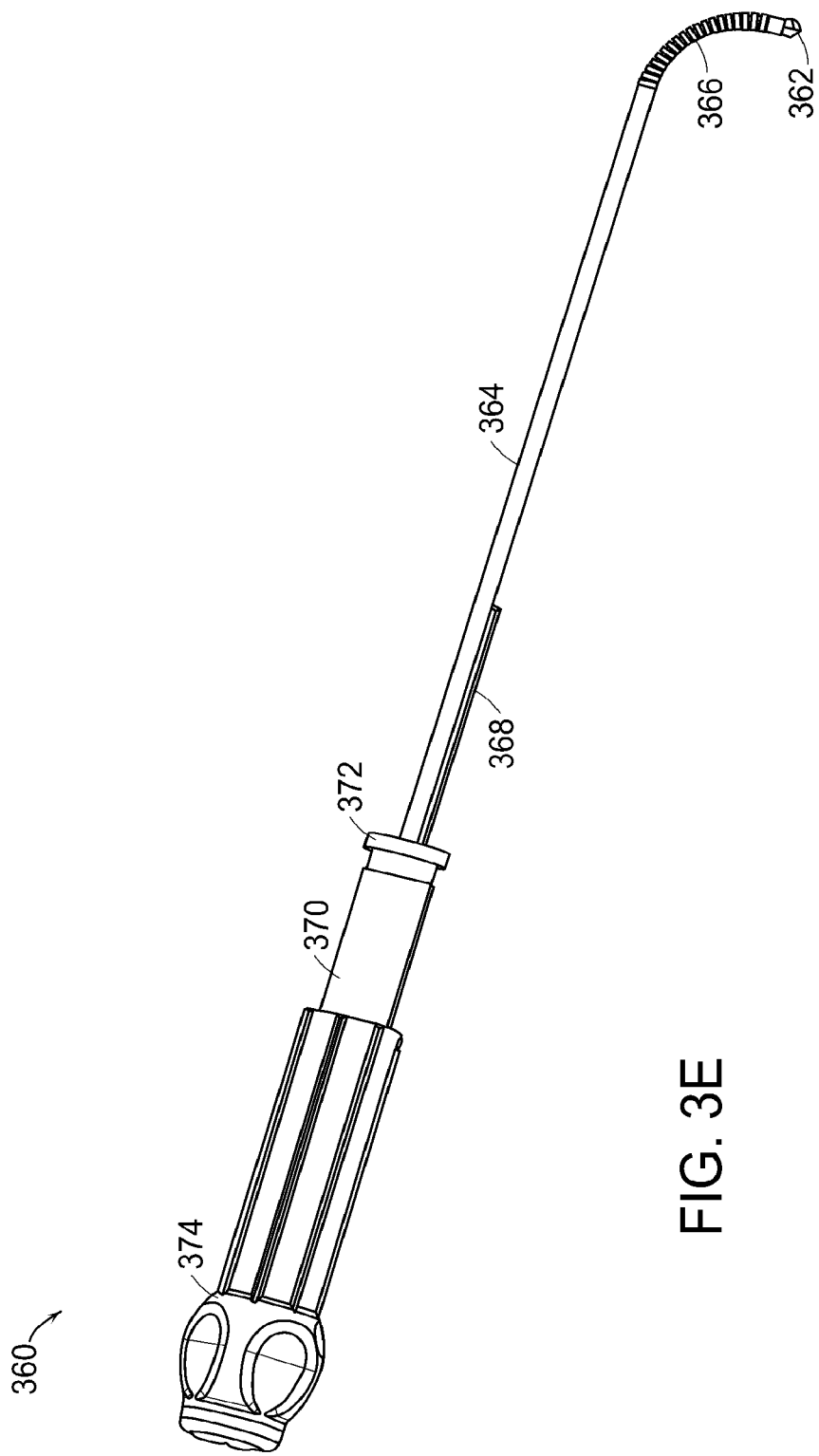
FIG. 3E is a schematic perspective view of another drill assembly, in accordance with one embodiment of the invention.

Another example of a curved drilling device is shown in FIGS. 3E-3I. As shown in FIG. 3E, the curved drilling device 360 can include a drill tip 362, a drill shaft 364 with a slotted portion 366 at the distal end for bending, an orientation key 368, a drill feed unit 370 complete with a locking flange 372 and a handle 374 for rotation.

The curved drilling device 360 releasably attached to a cannula and handle assembly 220 is shown in FIG. 3F. In one embodiment of the invention, when the curved drilling device 360 is initially installed into the cannula 376, the protrusion is only that of the drill tip beyond the cannula and as such, the slotted portion of the drill shaft is contained in the cannula and is therefore straight and not curved. The distal end of the drilling device 360 is free to curve once it has been deployed beyond the distal end of the cannula.

Figure 3H:
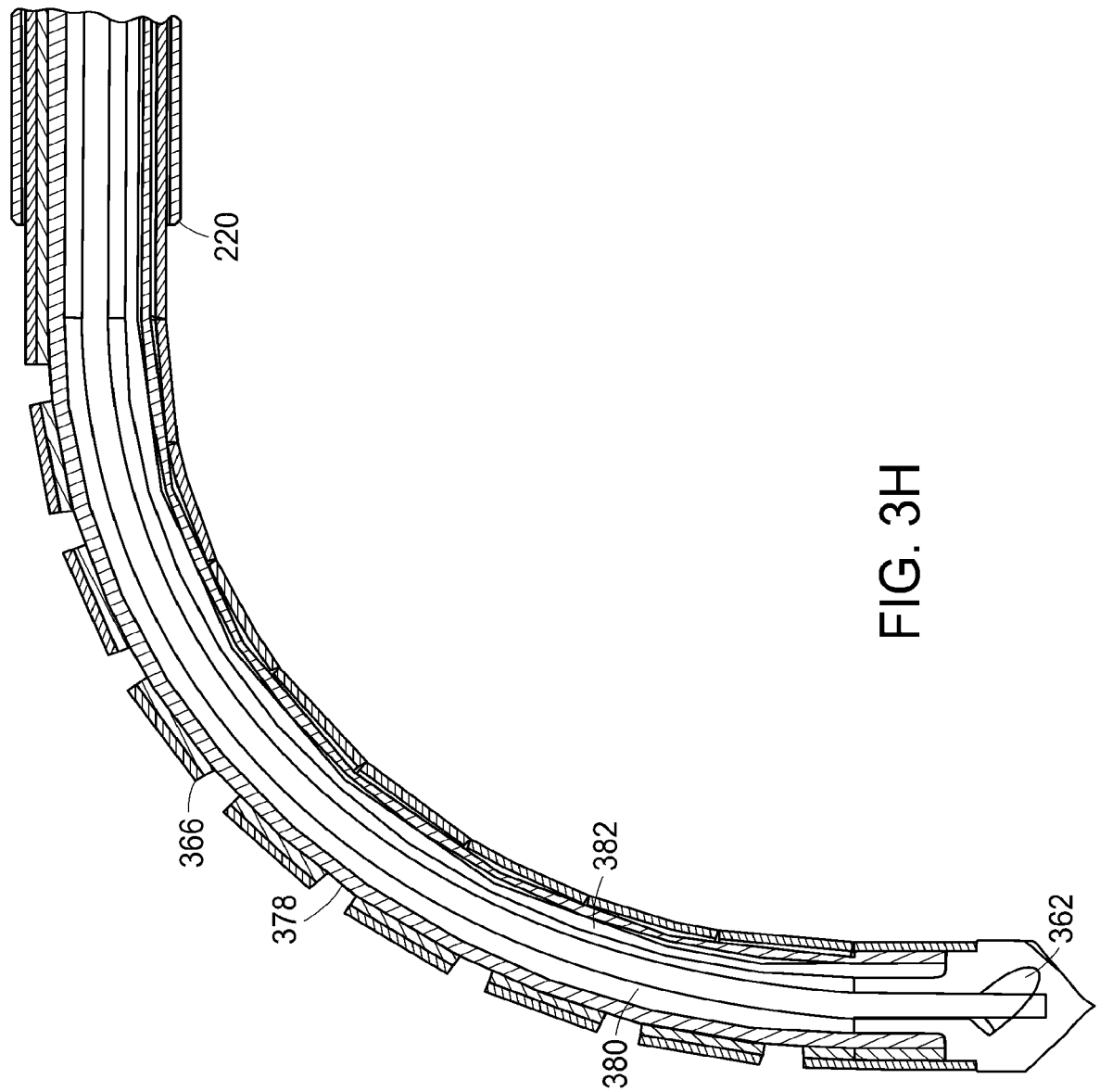
FIG. 3H is an enlarged sectional side view of the distal end of the drill assembly of FIG. 3E.

A cross-section of the curved drilling device 360, depicting the internal mechanisms of the system, is shown in FIG. 3G. More detailed enlarged cross-sectional diagrams are provided in FIGS. 3H and 3I. In FIG. 3H the distal end of the drill unit is illustrated. In this embodiment, the drill tip 362 can be welded, bonded, threaded, or otherwise coupled, to a cabled torque tube 378 that provides rotation of the tip 362. The torque tube 378 may be an array of wires wound in a helical, circular manner that provides torque strength with the flexibility to "go around the corner" to deliver the necessary power to the drill tip 362 to cut bone. A drill safety cable 380 can be coupled to the drill tip 362 to promote drill tip retrieval in the unlikely event that it becomes detached from the cabled torque tube 378.

The slotted portion of the drill tube 366 is bent into a desired arc as it exits the cannula. This is achieved by means of the band 382, located on the inside of the bend and firmly attached to the drill shaft 364 at its distal end and attached to a compression spring assembly 384 at its proximal end. As a result, the band 382 can be held under spring tension, thus pulling on the inside of the drill shaft 364 to produce an arc, as desired.

Figure 3I:
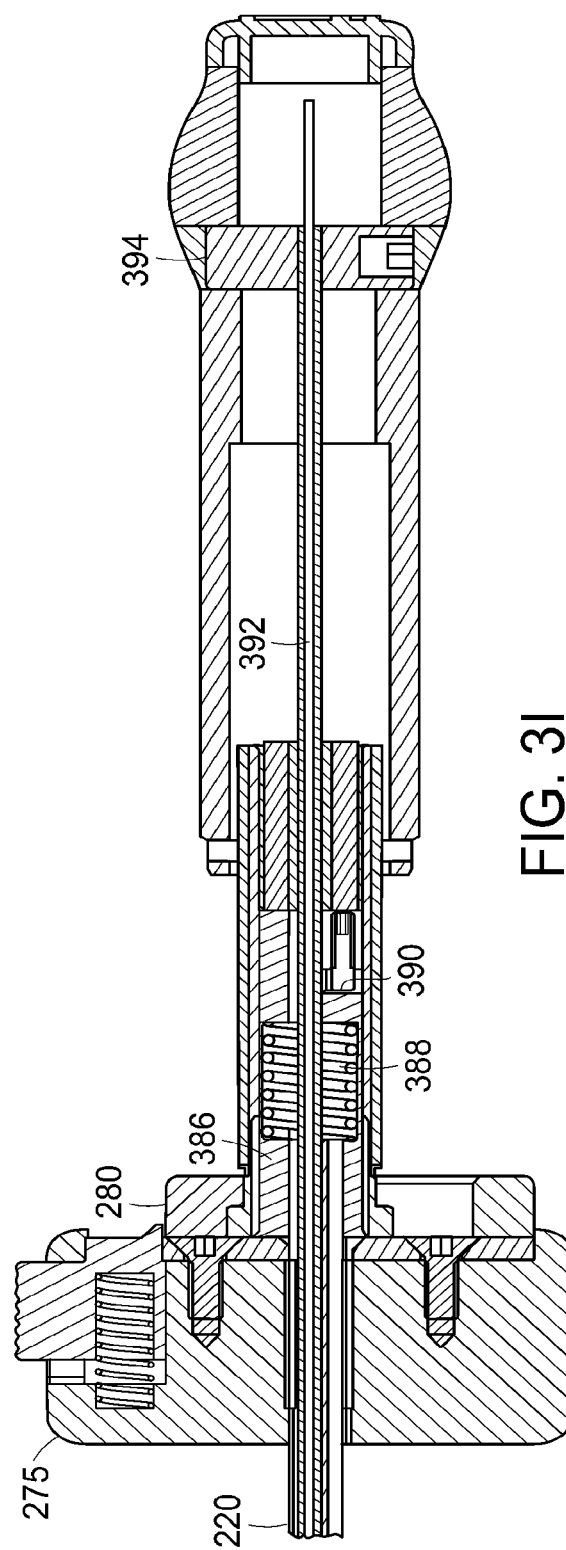
FIG. 3I is an enlarged sectional side view of the proximal end of the drill assembly of FIG. 3E inserted within a cannula.
Figure 3J:
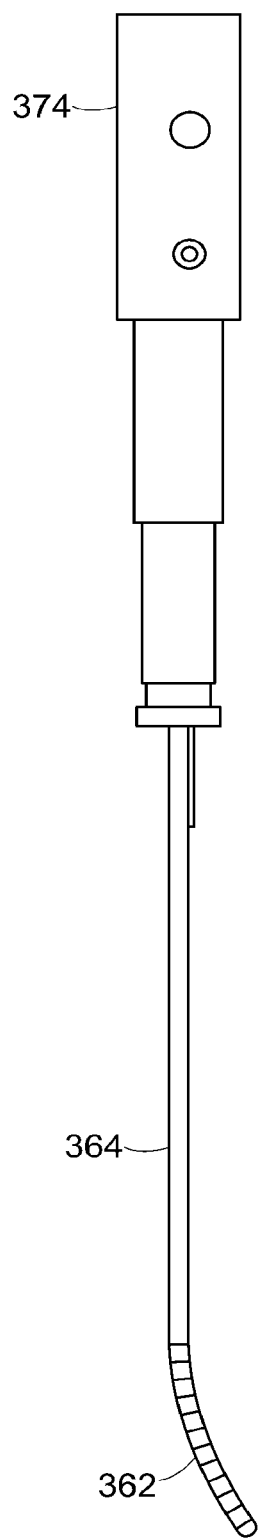
FIG. 3J is a schematic plan view of a drill assembly, in accordance with one embodiment of the invention.
Figure 3K:
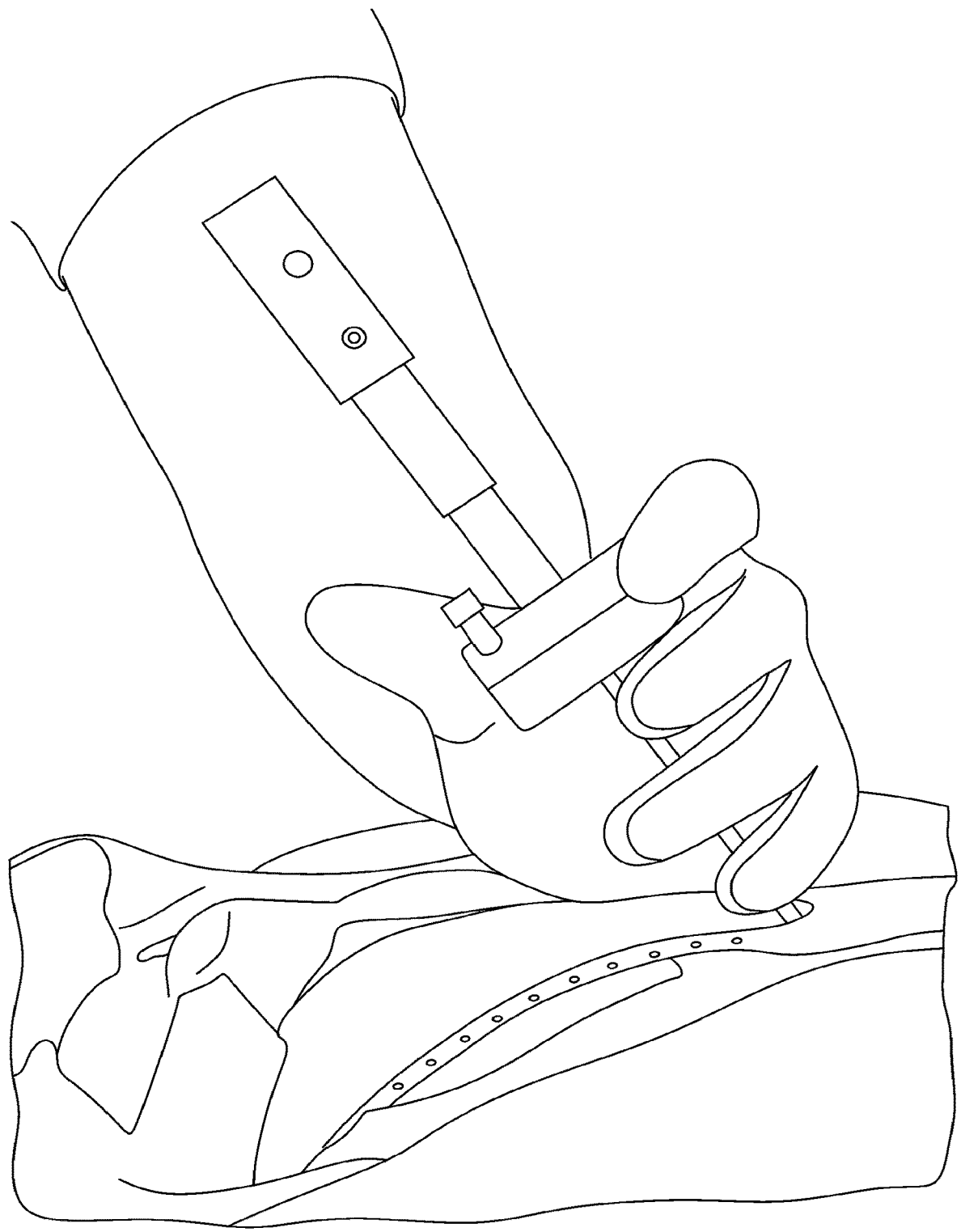
FIG. 3K is a picture of a drill assembly being inserted into a patient, in accordance with one embodiment of the invention.

FIG. 3I is a detailed cross section of the drill unit and handle, in accordance with one embodiment of the invention. In one embodiment, the locking flange on the drill unit can be retained by the locking flange of the handle. That, in turn, can be held in place by the locking slide 280 on the handle. The locking flange component can also have an internal thread or drill feed nut.

In one embodiment of the invention, a feed screw 386 includes a matching male thread. The proximal end of the drill shaft can be affixed to the feed screw 386 by welding, bonding, threading, or other means, and the feed screw 386 and drill shaft can have a key, also attached by welding or other means, to ensure the desired circumferential orientation of the drill shaft within the cannula 220. The key interface can align the handle plane to the plane of the curved drill shaft. One embodiment can also include a compression spring 388 for providing a pulling force on the band in order to bend the distal end of the drill shaft to the desired arc. A band retention device 390 can contain the compression spring 388. The compression can be preloaded to a desired force and the band retained to ensure that there is always tension on the band. In one embodiment of the invention, the spring 388 may be compressed as the band is pulled distally to allow for straightening of the drill shaft when passing through the cannula.

In one embodiment, the torque tube 392 can go through the drill shaft and feed screw, as well as through the band retention device, and be fastened to the handle 374 by the torque retention device 394 that is keyed to the rotation handle 374. The drill safety cable can go through the entire length of the torque tube and the excess can be tied into a knot. Alternatively, a ferrule can be staked to the drill safety cable so that it does not slide out of the torque tube inadvertently.

In operation, according to one embodiment of the invention, as the handle 374 is rotated the pins in the handle interact with the slots in the drill feed unit and cause it to rotate. This action causes the feed screw to move and advance the drill while rotating the drill tip 362 for cutting. This motion allows the drill tip 362 to cut a curvilinear path through the interior of the vertebral body. The progress of the pathway can be monitored by use of a medical imaging technique, or be measured by means of a distance scale associated with the drill and indicating the extension of the drill tip beyond the end of the cannula.

An example embodiment of a drill assembly can be seen in FIG. 3H. An example of this drill assembly inserted into a patient can be seen in FIG. 3I.

Reamer

In one embodiment of the invention, the curved path created by the drill device can be enlarged by a reamer device. Enlarging the cavity can allow it to accommodate the stent and that medical cement that will ultimately be injected into the cavity. An example of a reamer device is shown in FIGS. 4A-4G.

In one embodiment, the distal end of the reamer is configured for insertion through a cannula into a vertebral body. The reamer can include an orientation key configured to mate with a corresponding slot in the cannula to ensure that the distal end of the reamer is deployed at the correct circumferential angular orientation. The reamer may be releasably lockable in the cannula.

In one embodiment, the reamer can include a circumferentially partially slotted outer tube, wherein the slots enable the distal end of the reamer to bend in a predetermined direction. The reamer may include a band inserted within the outer slotted tube and coupled to the distal and the proximal ends of the reamer to bend the slotted outer tube in a predetermined direction and at a set angle. The proximal end of the band may be coupled to a compression spring to provide a predetermined amount of flex to the distal end of the reamer, thus allowing the distal end to be straightened while being inserted through the cannula, and then return to its predetermined bent configuration upon being extended beyond the end of the cannula.

The reamer may include a reamer blade yoke configured to extend from the distal end of the outer slotted tube. A reamer blade may be pivotably coupled to the reamer blade yoke by a pivot pin. The reamer may include a cabled torque tube coupled to the reamer blade yoke to rotate the reamer blade yoke and coupled reamer blade while the outer slotted tube remains stationary. A cable may be extended through the cabled torque tube and coupled to the reamer blade to provide a force to pivot the blade about the pivot point from a neutral, centered configuration to a tilted/opened configuration. The cable may be attached, at the proximal end of the reamer, to a compression spring. The compression spring attached to the cable can eliminate slack in the cable and allow the angle of the reamer blade to elastically deflect from its set angle.

In one embodiment, the proximal end of the reamer may include a handle. The handle may include a blade opening sleeve. Rotation of the blade opening sleeve can open or close the reamer blade with or without rotating the blade. The handle may also include a rotation handle. Rotation of the rotation handle can rotate the reamer blade about the reamer blade yoke. Rotation of the rotation handle can also provide a proximal movement of the distal end of the reamer back towards the distal end of the cannula;

In operation, in one embodiment of the invention, rotation of the reamer blade, while opening the blade, results in a semi-spherical cavity being created. Once the blade is fully opened, rotation of the rotation handle provides a rotational movement and a proximal movement of the reamer blade, allowing the reamer blade to follow a generally helical path to create a curved, generally cylindrical cavity of a length determined by the amount of rotation of the rotation handle. The proximal end of the reamer may include markings to indicate the amount of proximal movement of the distal end of the reamer from an original, fully extended position. Rotation of the blade opening sleeve in the opposite direction can return the reamer blade to a neutral/centered orientation. Upon returning the reamer blade to the neutral/centered orientation, the reamer may be unlocked and removed from the cannula.

In one embodiment, the reamer device may be similar in construction to the drill devices described above. Both devices can have a slotted tube assembly and a flexible torque transmitting drive shaft contained therein. Both devices can have an internal tube welded, bonded, or otherwise coupled at the distal end, and joined by a washer and compression spring at the proximal end. However, the reamer device can have a moveable blade disposed at its tip. The moveable blade can be attached to a yoke by a pivot pin, and to a cable tether that is crimped, bonded, welded, or otherwise attached to the moveable blade at a location distal to the pivot pin.

Figure 4A:
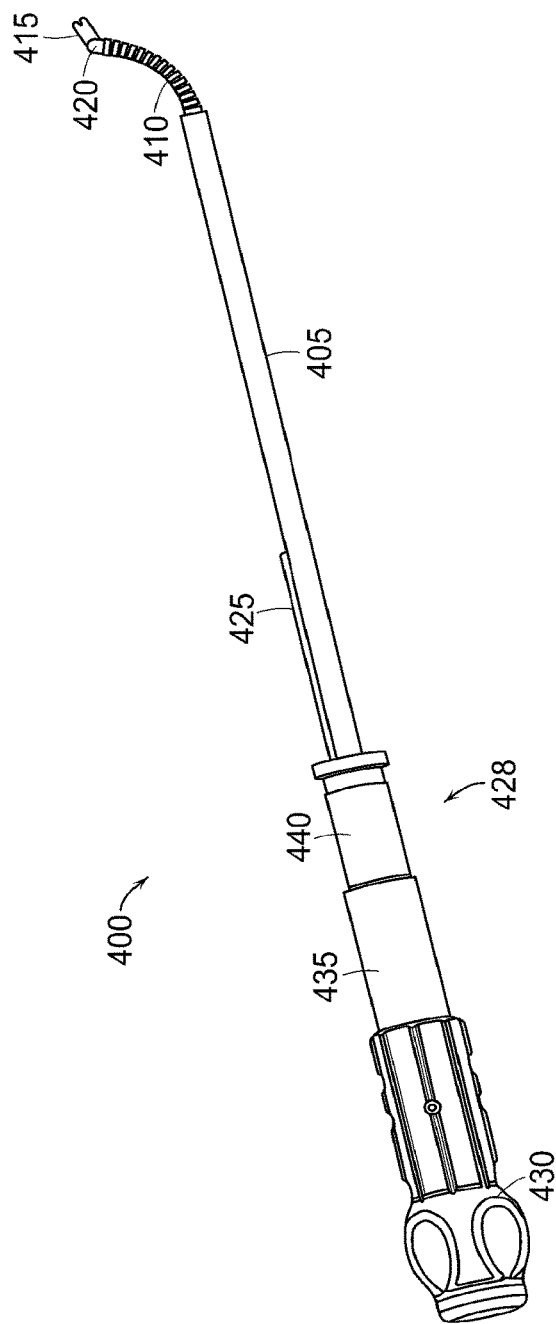
FIG. 4A is a schematic perspective view of a reamer assembly, in accordance with one embodiment of the invention.

More specifically, a reamer device 400 for enlarging the drilled cavity to a desired diameter and curvilinear length is shown in FIG. 4A. The reamer device 400 may have similarities to the drilling device described above in that it has a shaft 405 that is slotted at the distal end 410 for curving, and the curving is produced by a band that is spring loaded by a compression spring situated between the feed screw and the band retention device. In this embodiment, the reamer device 400 includes a reamer blade 415 that is pivotably coupled to a yoke 420 that is mounted on the distal end of the shaft 405. An orientation key 425 may be mounted to the shaft 405 to engage with a slot in a cannula and ensure the correct circumferential orientation of the reamer device upon insertion. At its proximal end, the reamer device 400 can include a dual function handle 428 including rotation handle 430 for rotating the blade 415, a blade opening sleeve 435 for deploying the blade, and a reamer feed nut 440 for moving the blade back and forward along the axis of the shaft as the blade is rotated. The proximal end of the handle 430 may be a tubular molded component with gripping features on its external surface. In an alternative embodiment, the handle 430 may be manufactured from any appropriate metal, plastic, ceramic, composite material, or combination thereof. Rubber or fabric elements may also be placed on the outer surface of the handle 430 to promote grip.

Figure 4B:
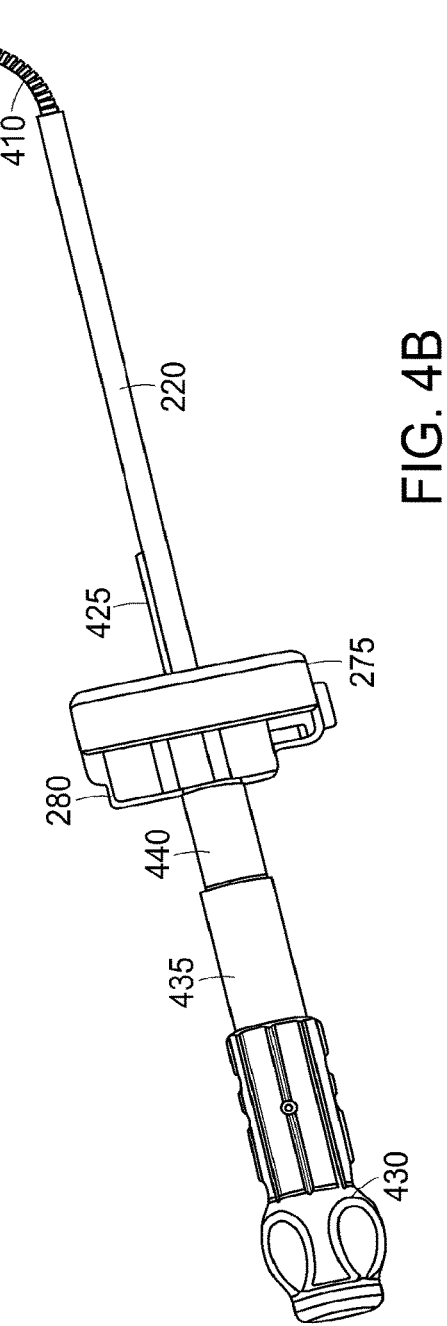
FIG. 4B is a schematic perspective view of the reamer assembly of FIG. 4A inserted within a cannula, in accordance with one embodiment of the invention.

The reamer device 400 releasably attached to a cannula and handle assembly 220 is shown in FIG. 4B. A cross section of the reamer device 400, depicting the internal mechanisms of the system, is shown in FIG. 4C. More detailed cross-sectional diagrams are provided in FIGS. 4D and 4E.

In one embodiment, the reamer assembly may also be retained in the cannula and handle assembly 220 in the same manner as described above for the drilling device. The reamer feed nut 440 may work in the same way as described above for the drilling device feed nut. In one embodiment, a torque tube 445 can provide power for reaming (enlarging) the drilled hole, with the torque tube 445 driving the yoke 420 that houses the pivoting reamer blade 415. An inner cable 450 that goes through the center of the torque tube 445 can be used to tilt or open the blade 415 from the neutral position aligned with the axis of the shaft 405 to a deployed position at an angle to the axis of the shaft 405. The blade 415 can tilt or pivot about a pivot pin 455 coupled to the reamer blade yoke 420. As with the drilling device above, the curvature of the distal end of the reamer device 400 can be set by a band 460 placed within the slotted tube 410 and held in tension by a spring element at the proximal end of the reamer device 400. The fully deployed angle may be set at any appropriate angle. In one embodiment, the deployment angle may be set at any angle up to 90°. For example, the fully deployed angle may be in a range from 20° to 90°, or from 30° to 70°, or from 45° to 60°.

The curvature of the distal end may be set to any appropriate angle by correct selection of the band length. A band retention device 462 can hold the band 460 at the proximal end of the reamer device 400, with a compression spring 464 coupled to the band retention device 462 to allow the shaft 405 to flex from its preferred steady state curvature during deployment through the cannula 220 and upon contact with a "hard" element within the vertebral body.

Figure 4E:
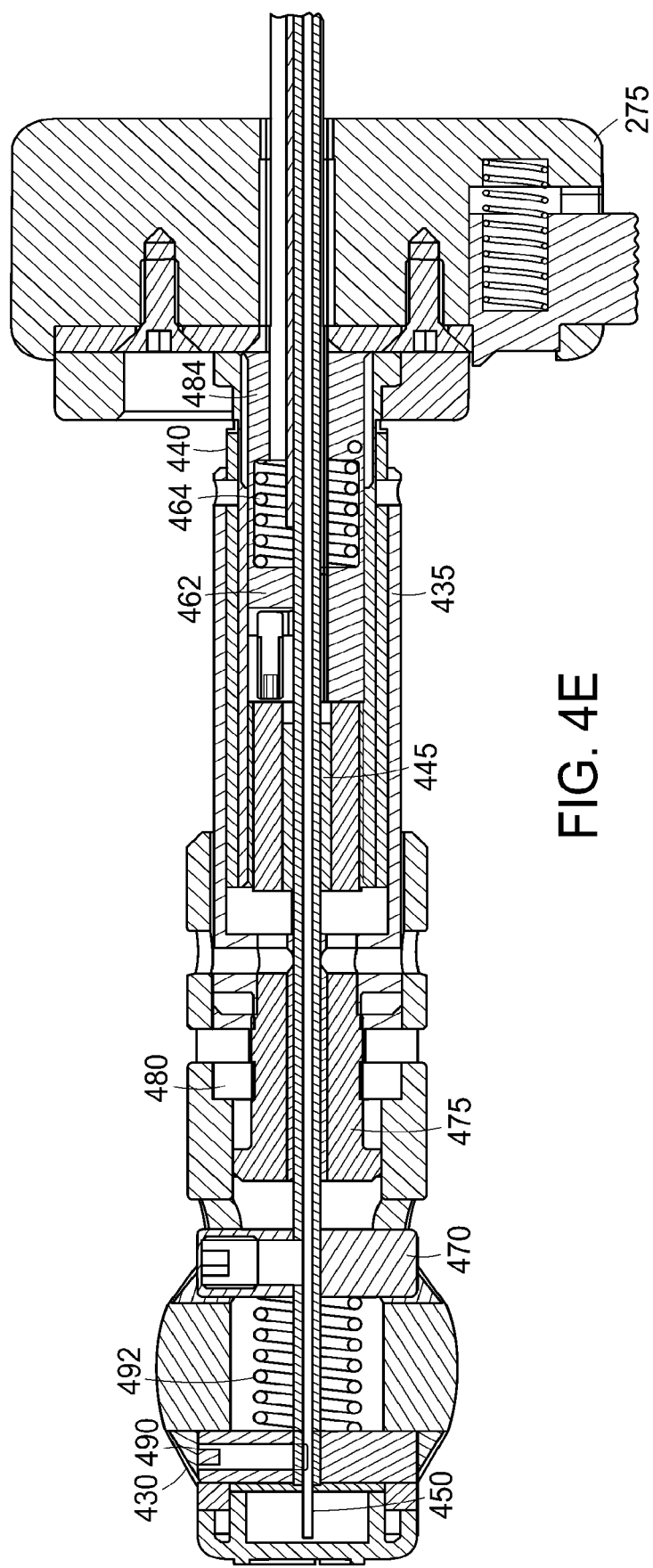
FIG. 4E is an enlarged sectional side view of the proximal end of the reamer assembly of FIG. 4A inserted within a cannula.

The reamer device 400 can include a multi-component, dual function handle. A cross-section of an example handle is shown in FIG. 4E. In one embodiment of the invention, a lost feed motion may be needed to open the reamer blade, while rotating the reamer handle, with the feed system remaining still. This feature is provided by means of a blade opening sleeve 435. In one embodiment, this may be achieved by a rotation of the handle to initially "telescope" the handle from the blade opening sleeve 435 to pull on the center cable 450 to open the reamer blade 415 all while no feeding motion occurs. A torque tube retention device 470 travels in an elongated slot in the rotation handle 430 so no proximal movement results. The blade opening sleeve 435 retains a "T" screw 475 that provides the proximal movement of the handle for blade opening and when a blade opening nut 480 stops on the head of the T screw 475, rotation is now transferred to the reamer feed nut 440.

The reamer feed nut 440 rotation pulls the feed screw 484 proximally and at the distal end the reamer blade is rotating and feeding proximally resulting in cutting bone and creating a curved cavity to desired length with fluoroscopy, or other appropriate means, for visual reference. After the desired length of cavity has been achieved, the rotating handle 430 is rotated counter to the cutting direction and the reamer blade 415 will fold back inward to the center starting position. The reamer assembly can be unlatched from the handle and removed. The cannula and handle assembly 220 can remain in place, however, so that further devices, such as devices that permit the insertion of the stent and the medical cement, can be inserted into the enlarged cavity.

The cable 450 originating from the moveable blade may be fed through the entire assembled device and terminated and crimped, or otherwise coupled, to a cable retainer 490, such as a cross pin assembly, that is coupled to the wall of the rotation handle 430. A spring 492 may be located within the proximal inner border of the rotation handle 430 adjacent to the cable retainer 490. A thread may by used to couple the rotation handle 430 to the remainder of the reamer device 400.

In one embodiment, the dual function handle 428 may induce a tensile force on the cable tether 450 by rotating the proximal molded component relative to the distal handle component to effectively lengthen the handle. The cable tether thereby pulls the moveable blade 415 to cause a pivoting of the blade from a closed to an open position. The handle 428 can then cause the rotation of the flexible drive shaft assembly to rotate the blade 415 within the cavity.

The handle assembly, including the distal and proximal components, may be further secured to a rotator component having an internal thread mating the feedscrew component 484 of the slotted tube assembly. Thus, its function may be substantially identical to that of the drilling device described above. However, the feedscrew rotation may not be enabled until the reamer blade has been fully deployed via rotation of the proximal component of the handle 428. Therefore, in one embodiment, when the rotation handle 430 is rotated, the moveable blade assembly first rotates and deploys, then translates due to the action of the feedscrew mechanism 484. The deployed blade therefore enlarges the path to a required diameter by simultaneously rotating and translating the blade 415. The direction of translation, in one embodiment, is retrograde, which is achieved by the use of a left hand thread in the feedscrew 484.

In one embodiment, the blade deployment from a neutral to an open position may only occur when the blade is rotating. In an alternative embodiment, the blade deployment may be independent of the blade rotation. The rate of blade deployment from a closed to an open position is dependent on the pitch of the thread which joins the proximal and distal handle component.

In an alternative embodiment, the reamer device may be configured to drill into the vertebral body as it is advanced, before being deployed to extend the size of the cavity, as described above. In this embodiment, the reamer device can function as both a reamer and a drill, thus eliminating the need for a separate drilling device.

Figure 4F:
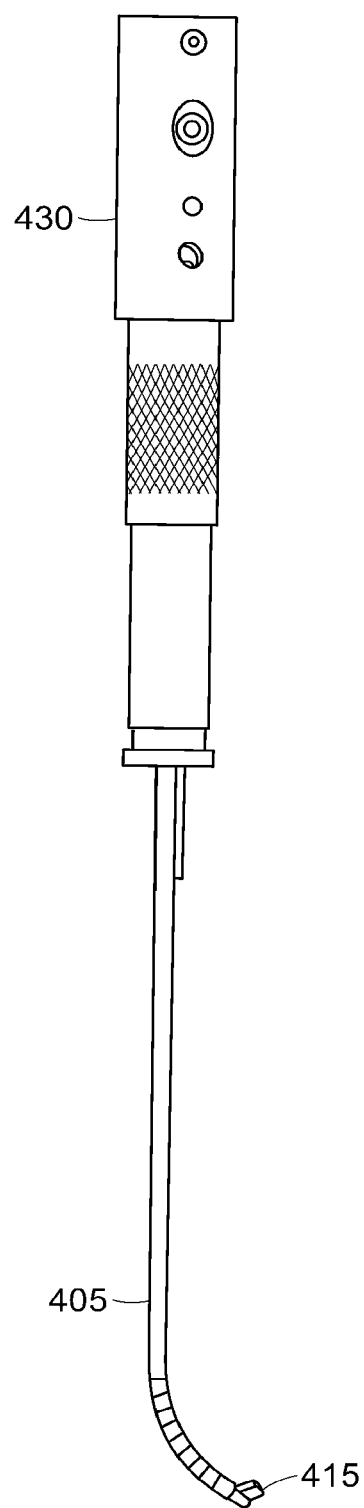
FIG. 4F is a schematic plan view of a reamer assembly, in accordance with one embodiment of the invention.
Figure 4G:
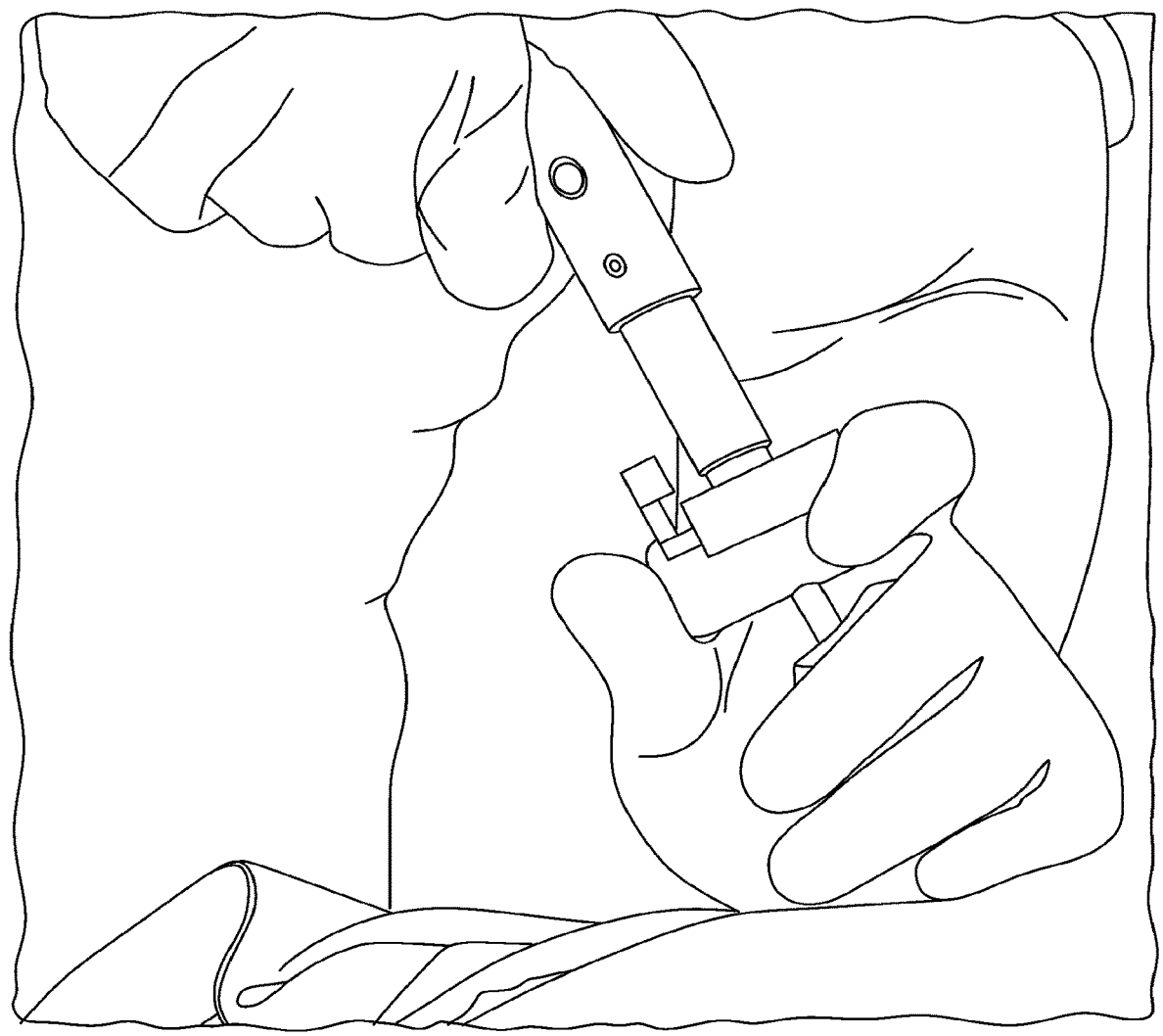
FIG. 4G is a picture of a reamer assembly being inserted into a patient, in accordance with one embodiment of the invention.

An example embodiment of a reamer device can be seen in FIG. 4F. An example of this drill assembly inserted into a patient can be seen in FIG. 4G.

Method of Use

The devices discussed herein may be used in conjunction to provide a method of creating a curvilinear cavity within a vertebral body, or other bony structure. As disclosed herein, the creation of a curvilinear pathway and cavity within a vertebral body allows the cavity to extend over a potentially larger region of the interior of a vertebral body, and bisect an axis of the vertebral body using only a single point of access. After creation of a cavity in a damaged or diseased vertebral body, the cavity can be filled with a medical cement or other treatment element to stabilize the vertebral body and alleviate pain. As a result, the creation of a curvilinear pathway and cavity using these devices can enable the complete stabilization of a vertebral body from a single access incision, thus reducing the time needed for a surgical procedure and the damage caused to surrounding tissue and bone during a procedure. This can greatly improve the efficiency and safety of such a procedure.

In one embodiment of the invention, a procedure for using the devices disclosed herein can be used to produce a curvilinear cavity within a vertebral body. One example embodiment of the invention further includes a method of placing a stent within a vertebral body. The stent can be a self-expanding, covered stent that allows interdigitation and prevents leakage of bone cement in undesired directions. In one embodiment, a single stent can be placed at a mid-line location of a vertebral body, rather than placing multiple stents on either side of the mid-line, thus reducing the time and fluoroscopy exposure require during a surgical implantation procedure.

In one embodiment, the method of creating a cavity for within a vertebral body, or other bony body, can include first creating a posterior pathway to the vertebral body, using a extrapedicular or intrapedicular approach, with a Jamshidi needle and/or K-wire. This may be performed, for example, using a dual C-arm technique to place and medialize the Jamshidi needle/K-wire to the fullest extent.

A working channel and trocar assembly can then be inserted along the pathway created by the Jamshidi needle/K-wire. This can be performed, for example, by locking the trocar into the working channel, inserting the working channel into the pathway, and tapping the assembly into place until the distal tip of the trocar and working channel extends, in one embodiment, 1-3 mm beyond the posterior wall of the vertebral body. The trocar can then be removed, leaving the open working channel in place.

A curved pathway through the vertebral body can then be created using a curved drill. This may be achieved using any of the drill arrangements described herein. In one embodiment, the drill depth markings at the user interface are set to "0" mm prior to insertion into the working channel. The drill can then be locked into the working channel with the key facing in the medial direction, thus ensuring the correct direction of curvature of the drill within the vertebral body. The handle of the drill can then be rotated to advance the drill tip into the vertebral body, with fluoroscopy, or some other appropriate technique, used to determine when the desired depth of penetration is achieved. The drill can then be removed and the depth markings on the user interface recorded. In one embodiment, the drill tip is oriented in the contralateral anterior quadrant of the vertebral body, thus assuring proper cavity positioning and bilateral cement filling.

In one embodiment, a larger cavity can then be created within the vertebral body by reaming out the hole created by the curved drill with a curved reamer. This may be achieved, for example, by first setting the depth markings on the user interface of the reamer to match those recorded for the drill depth, thus assuring that the reamer is positioned correctly within the vertebral body. The reamer can then be advanced fully into the pathway created by the drill and locked into the working channel, with the position of the reamer confirmed using fluoroscopy or some other appropriate technique. The blade of the reamer can then be opened, for example by rotating a portion of the handle of the reamer, and reaming can be carried out by rotating the handle. In one embodiment, the reamer may be stopped approximately 1-3 mm before approaching the distal tip of the working channel, with the position confirmed by fluoroscopy, or some other appropriate technique. The blade can then be closed (for example by rotating a portion of the handle in the opposite direction), and the reamer removed. In one embodiment, due to blade deflection, the cavity created by the reamer can have a slight taper from the distal end to the proximal end.

Once a cavity has been created, a stent delivery system can be locked into the working channel to correctly position a stent within the vertebral body. Once the stent has been positioned, a sheath covering the stent can be removed to deploy and expand the stent, and cement can be injected into the stent by attaching a syringe to the proximal end of the delivery system. The desired amount of cement can be injected into the stent with fluoroscopy, or some other appropriate technique, being used to monitor the flow of cement into the stent. Once the requisite amount of cement has been injected, the stent can be released from the delivery system and the delivery system removed from the working channel, thus leaving the stent in place within the vertebral body. The working channel can then be removed and the access pathway sutured or otherwise closed.

Figure 5A:
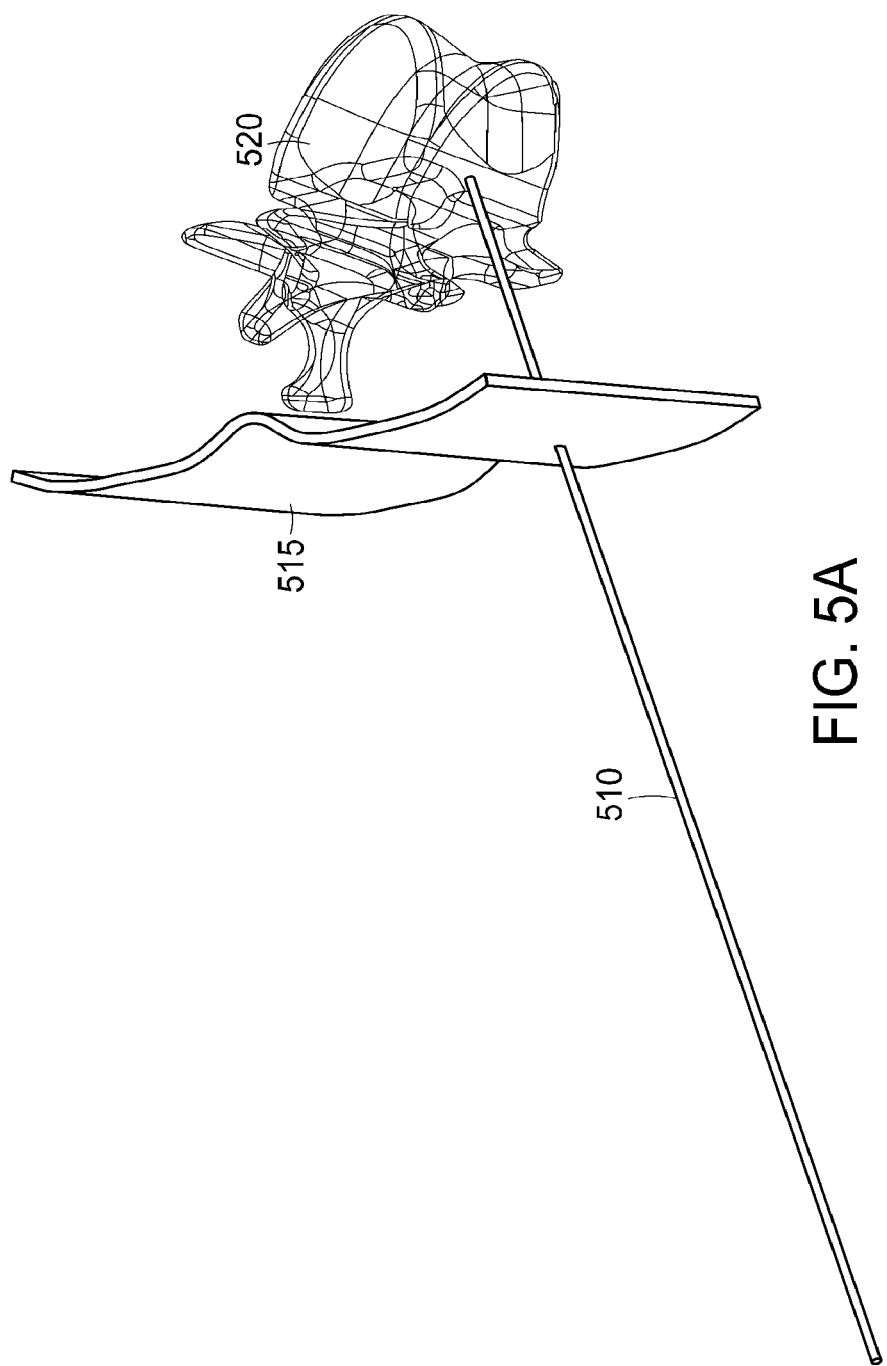
FIG. 5A is a schematic perspective view of a needle being inserted into a vertebral body, in accordance with one embodiment of the invention.

In one example embodiment, the pedicle of the vertebral body is first located. A needle assembly is then inserted percutaneously from the posterior approach through the outer tissue and anchored into the bone of the vertebral body to a suitable depth. This needle or wire will provide a guide for subsequent instruments. In one embodiment, the needle is a 1.5 mm diameter stainless steel pointed wire, although in other embodiments any appropriate diameter and material of needle may be used. The needle may be solid or hollow, depending upon the specific requirements of the procedure. An example of a guide wire or piercer 510 being inserted through the outer tissue 515 of a patient and into a vertebral body 520 by a posterior approach can be seen in FIG. 5A.

Once the guide wire 510 is in place, a trocar can be inserted into, and releasably coupled to a cannula, and the resulting trocar and cannula assembly slid over the guide wire 510. The trocar impact knob can be tapped with a hammer or other instrument to force the trocar forward to enlarge the hole in the vertebral body and thereby force the tip of the trocar and cannula into the bone. Once the trocar and cannula assembly have been correctly positioned, the trocar and the guide wire can be removed, thus leaving the cannula in place on its own. This cannula can then serve as a delivery path into the vertebral body for subsequent instruments.

Figure 5B:
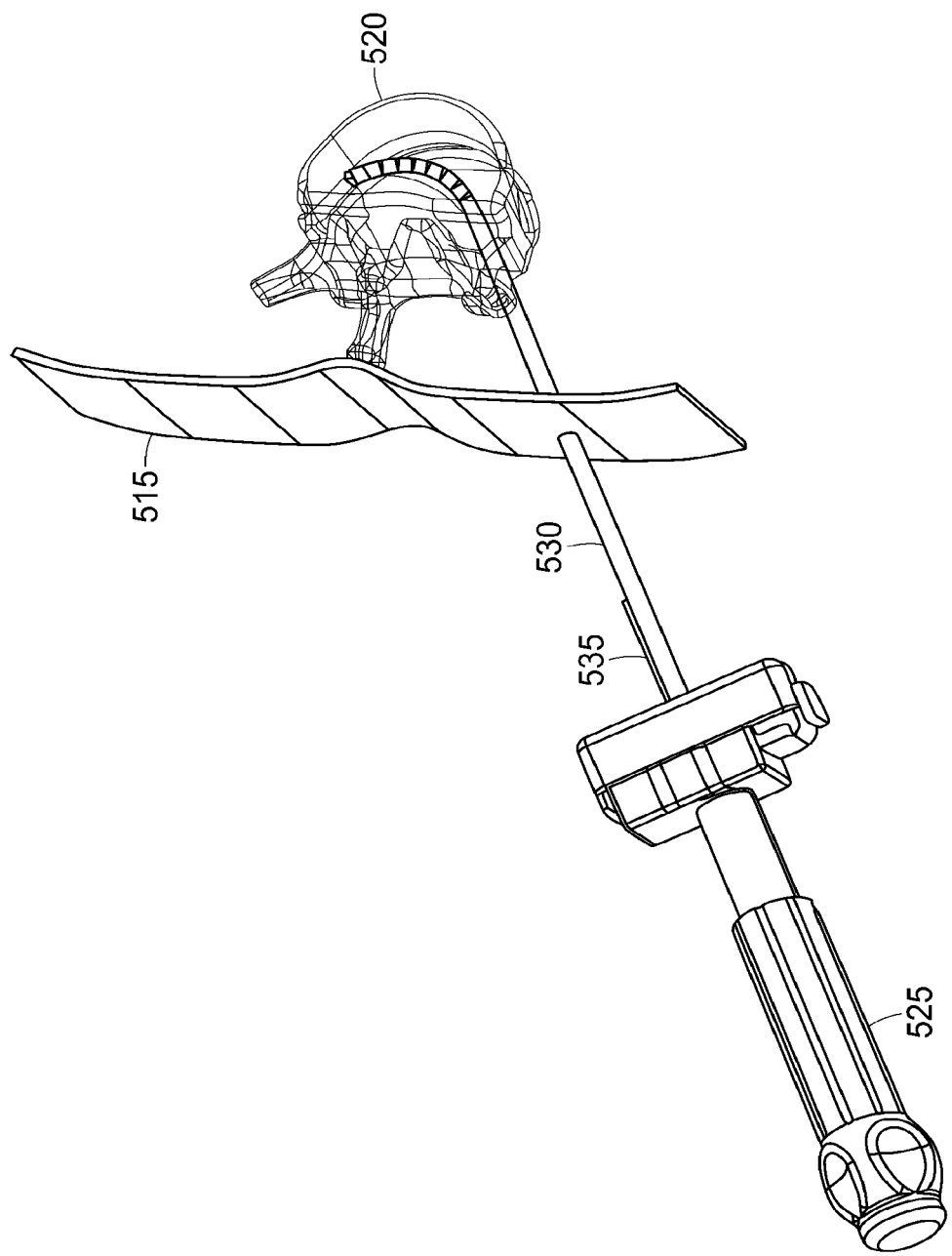
FIG. 5B is a schematic perspective view of a drill assembly being inserted through a cannula into a vertebral body, in accordance with one embodiment of the invention.

A curved drilling device can then be inserted through the cannula to create a curvilinear pathway through the vertebral body. An example of a drilling device 525 being inserted through a cannula 530 and into a vertebral body 520 can be seen in FIG. 5B.

The drilling device 525 can be slideably placed within the cannula by aligning the key on the drill 535 with the slot on the cannula. The drilling device 525 can then be fully inserted and releasably locked to the cannula 530 by sliding a locking tab to the lock position, or otherwise securing the drilling device 525 to the cannula 530. In this position, the curved slotted tube of the drilling device 525 is constrained in the straight tube of the cannula 530 and the sharp drill tip is positioned at the end of the cannula 530. After the drilling device 525 is secured to the cannula 530, for example by the locking the flange to the cannula handle, the drive handle of the curved drill can be rotated to cause the rotation of the flexible drive shaft assembly and sharp tip. Rotation of the flexible drive shaft assembly and sharp tip can also cause the simultaneous translation of the slotted tube and feedscrew assembly relative to the drive handle and cannula 530, thus translating the tip of the drilling device 525 into the vertebral body along a curvilinear path, provided the handle is locked to the cannula. For example, as it is being fed forward, the distal end of the drill shaft will begin to protrude from the cannula and starts to curve in the desired direction as it is cutting. The farther the drill shaft exits from the cannula, the greater the curved protrusion. As the drill tip rotates and travels in an arc, the resultant hole that it creates is also in an arc until the desired depth is achieved.

The sharp tip advances within the bone according to the pitch of the feedscrew. The advance of the tip of the drilling device 525 may be monitored fluoroscopically by the user, and/or the depth of drilling may be indicated by a scale printed or etched on the drilling device 525. When the path has been fully formed, the lock may be disengaged and the drilling device 525 removed from the cannula 530. The drilling device 525 can be removed by a counter rotation of the drill handle to withdraw the drill back into the cannula 530 and straighten the drill shaft in the process, after which the locking flange can be released and the drill assembly removed from the cannula 530. In an alternate embodiment, the drilling device 525 can be removed by simply unlatching it from the cannula 530 and pulling it out. This will, in turn, leave a hollow, curvilinear path through the vertebral body extending from the end of the cannula.

Figure 5C:
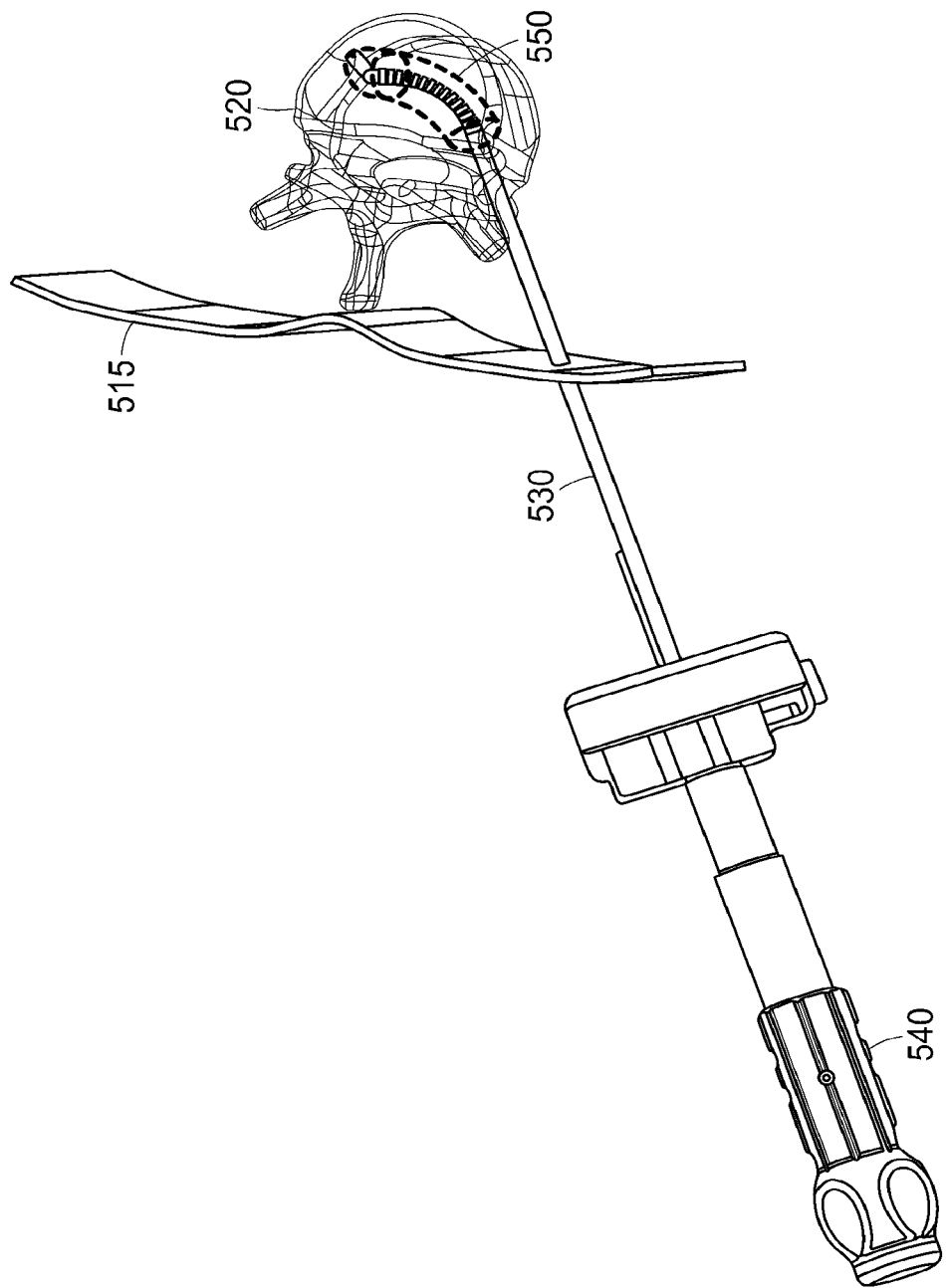
FIG. 5C is a schematic perspective view of a reamer assembly being inserted through a cannula into a vertebral body, in accordance with one embodiment of the invention.
Figure 6A:
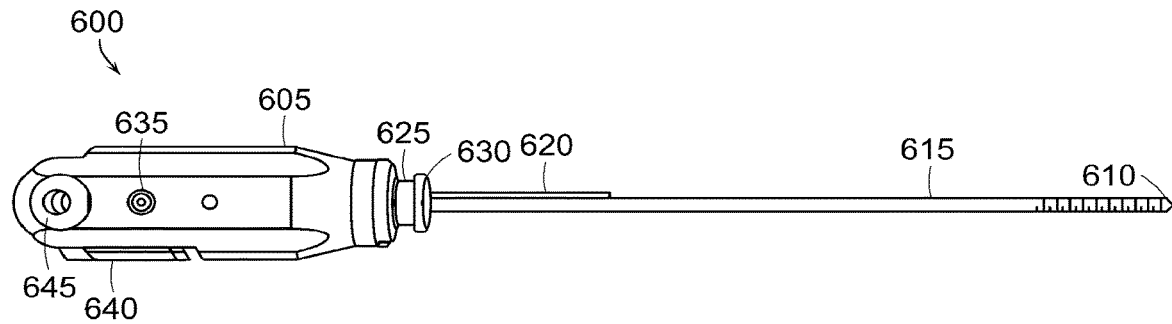
FIG. 6A is a schematic side view of a drill assembly with a lever and drill cam, in accordance with one embodiment of the invention.
Figure 6B:
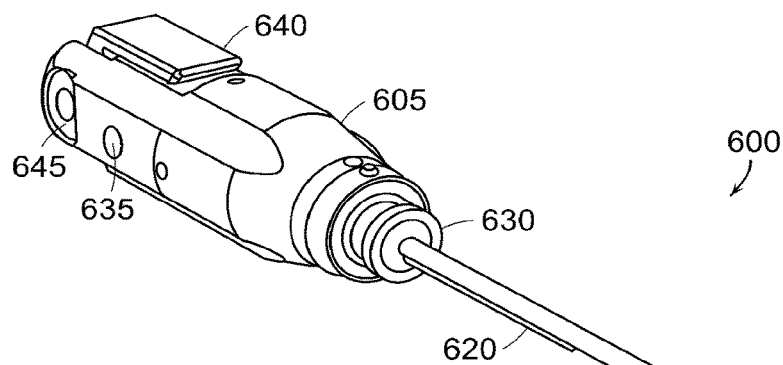
FIG. 6B is a schematic perspective view of the drill assembly of FIG. 6A.
Figure 6C:
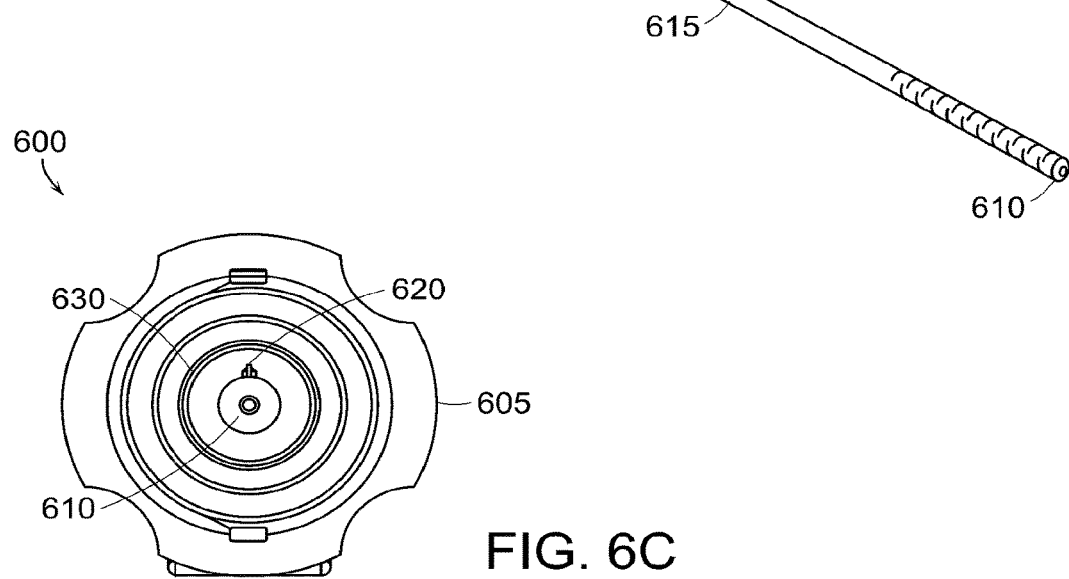
FIG. 6C is a schematic end view of the drill assembly of FIG. 6A.
Figure 6D:
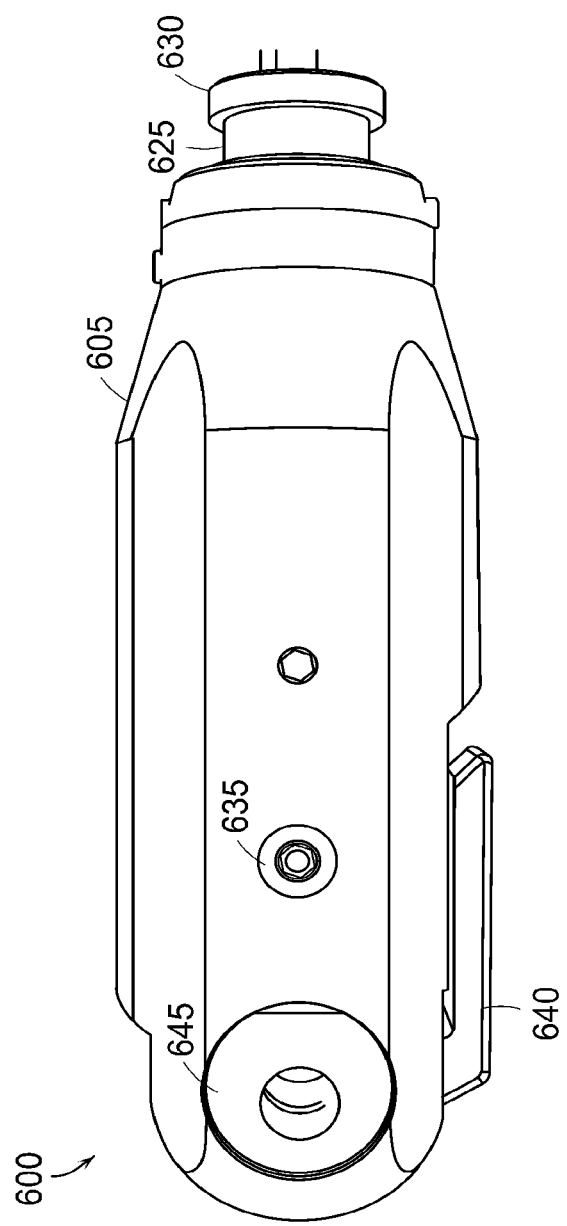
FIG. 6D is a schematic side view of the handle of the drill assembly of FIG. 6A.
Figure 6E:
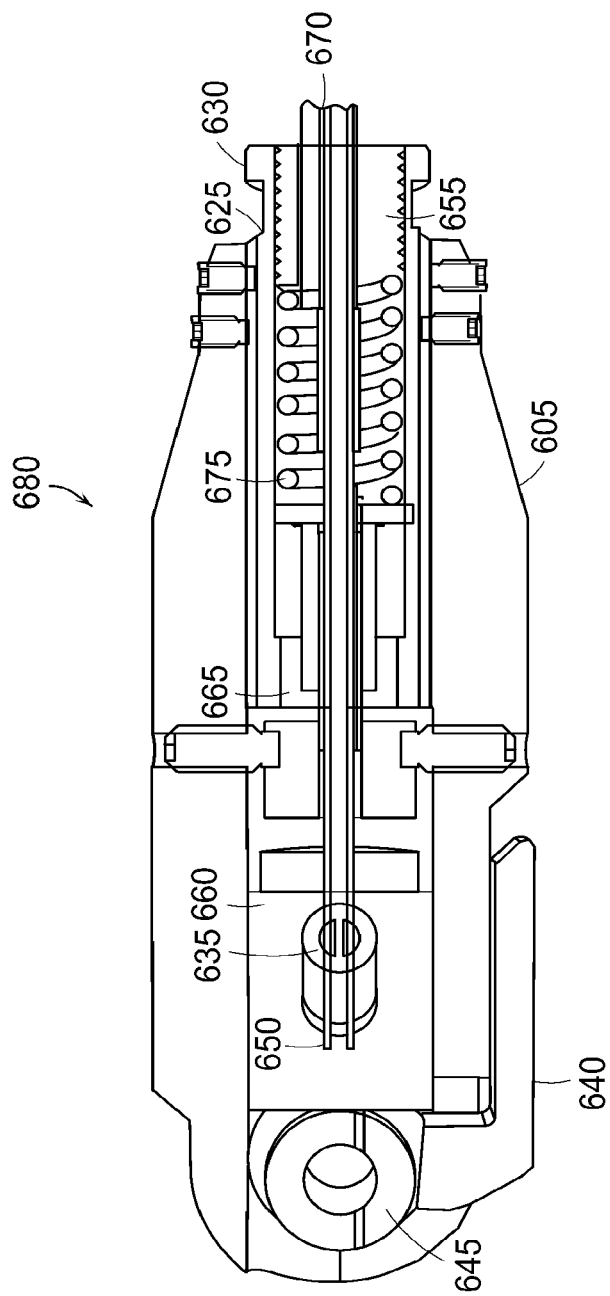
FIG. 6E is a schematic cross-sectional side view of the handle of the drill assembly of FIG. 6A through a central elongate axis of the drill assembly.

A curved reamer device can then be inserted through the cannula to enlarge the curvilinear pathway through the vertebral body created by the drilling device. An example of a reamer device 540 being inserted through a cannula 530 and into a vertebral body 520 can be seen in FIG. 5C.

The reamer device 540 can be preset to provide a desired protrusion, based on the depth of the path created by the drilling device, with reamer device 540 set to a depth that matches the drilled depth. The reamer device 540 can then be inserted through the cannula 530 to the full extent of the previously drilled cavity along the same circular path. The reamer device 540 can then be releasably locked or latched to the cannula 530. During insertion of the reamer device 540, the moveable blade of the reamer is set in an non-deployed position, located substantially along the axis of the shaft, so it may easily pass through the cannula 530. In one embodiment, the position of the reamer tip can fluoroscopically confirmed within the center of the vertebral body.

The handle of the reamer device 540 can then be rotated to deploy and rotate the blade, with the reamer blade pivoting outward from the shaft and cutting a semi-sphere to a desired diameter at the distal end of the cavity, without backward movement. This therefore forms a substantially semi-spherical terminus of a cavity in the bone at the end of the curvilinear path.

Once fully deployed, the blade can rotate and translate in retrograde fashion back toward the cannula 530 along a generally helical path in response to further rotation of the handle of the reamer device 540. The blade rotating action forms a generally curvilinear elongated hole. The speed of translation and cutting is dependent on the pitch of the feedscrew mechanism in the handle. The cavity created by the reamer device 540 may be monitored fluoroscopically to determine the length of the cavity, or the length may alternatively be monitored by a printed scale on the device.

When cavity cutting is complete, the proximal end of the handle may be counter rotated to relax tension on the tether cable and allow the movement of the blade back to the closed or non-deployed position. The reamer device can then be unlocked from the cannula 530 and removed. The resulting curvilinear cavity 550 is then free to have a treatment device, such as a stent and/or treatment material, such as bone cement, inserted into it.

The cannula 530 can then remain in place for insertion of other devices that will fill the cavity with medical cement. In one embodiment, these devices may include a stent and stent deployment apparatus, wherein the stent is filled with cement through the stent deployment apparatus to fill the curvilinear cavity and stabilize the vertebral body. After the cement injection procedure has been completed, the cannula 530 can be removed and the surgical incision closed.

Another embodiment of the invention can include a drill and/or reamer device including a lever and cam sub assembly or other mechanism to allow tension to be reduced in the spring assembly. This can allow the spring force providing the curvature to the drill or reamer to be reduced during insertion and/or removal of the elongated tube assembly and drill tip, thus easing the insertion and removal of the drill or reamer from the working channel during use. An example curved drill device 600 including a lever and cam sub assembly, with the distal end of the drill straightened, can be seen in FIGS. 6A through 6E.

In the embodiment shown in FIGS. 6A-6E, the curved drill device 600 can include a drive handle 605, a sharp drill tip 610 attached to a flexible torque transmitting drive shaft 650 positioned within a slotted tube assembly 615, and a handle drive assembly positioned within the handle 605. The slotted tube assembly 615 can be a spring loaded, flexible, slotted metal tube. A key component 620 can be located on the slotted tube assembly 615 to ensure that, during operation, the drill 600 is inserted and locked into the working channel, such as a hollow cannula, in the desired circumferential orientation. A drill feed nut 625 including a locking flange 630 can be threaded onto the handle drive assembly 680 located within the handle 605, with the locking flange 630 providing a locking element for releasably locking the drill 600 to a cannula. A cable retaining pin 635 can be inserted within, and keyed to, the handle 605 to provide a torque retention device to anchor the proximal end of the flexible torque transmitting drive shaft 650. The cable retaining pin 635 can then drive the shaft 650 as the handle 605 is rotated.

The handle drive assembly 680 within the handle 605 includes a feed screw 655 onto which the feed nut 625 can be threaded. The cable retaining pin 635 is located within a cam pusher assembly 660 located within the central portion of the handle 605. A band retention element 665 is used to anchor a band 670 located within the slotted tube assembly 615, and anchored at its distal end to a distal portion of the slotted tube assembly 615, to provide the force necessary to produce a curvature at the distal end of the drill 600. A compression spring 675 is positioned between the feed screw 655 and the band retention element 665 to provide a spring force to the band retention element, thereby allowing the curvature of the distal end of the drill 600 to flex.

In addition, the curved drilling device 600 includes a lever 640 attached to a drill cam 645 mounted on the proximal end of the handle 605, wherein the lever 640 pivots the drill cam 645 about a central axis upon actuation by a user. The drill cam 645 includes an eccentric inner portion that abuts against a cam pusher assembly 660 located within the central portion of the handle 605. The cam pusher assembly 660 abuts against the band retention element 665, or other intermediate element. The band retention element 665 provides a stop for the compression spring element 675 located within the central axis of the handle 605 and configured to provide a spring force to the band retention element 665, thus providing the required force to the band 650 in order to maintain the distal end of the slotted tube assembly 615 in a curved configuration.

In operation, when the lever 640 is closed against the handle 605 of the drill 600, the compression spring 675 pushes the band retention element 665 and cam pusher assembly 660 against the drill cam 645, and provides the force necessary to produce a curvature at the distal end of the drill 600. However, when the lever is pulled away from the handle 605, it pivots the drill cam 645 about its axis and, due to the eccentric configuration of the drill cam 645, forces the cam pusher assembly 660 and band retention element 665 against the spring element 675. This has the effect of compressing and foreshortening the spring element 675, thus reducing the force provided to the distal end of the slotted tube assembly 615 and therefore allowing the distal end of the slotted tube assembly 615 to be straightened with less or minimal effort.

In another embodiment of the invention, a reamer, such as any of the reaming devices described herein, could include a lever and cam sub assembly or other mechanism to compress and foreshorten a compression spring within the handle of the reamer, thus allowing the distal end of the slotted tube assembly of the reamer to be straightened with less or minimal effort.

Figure 7A:
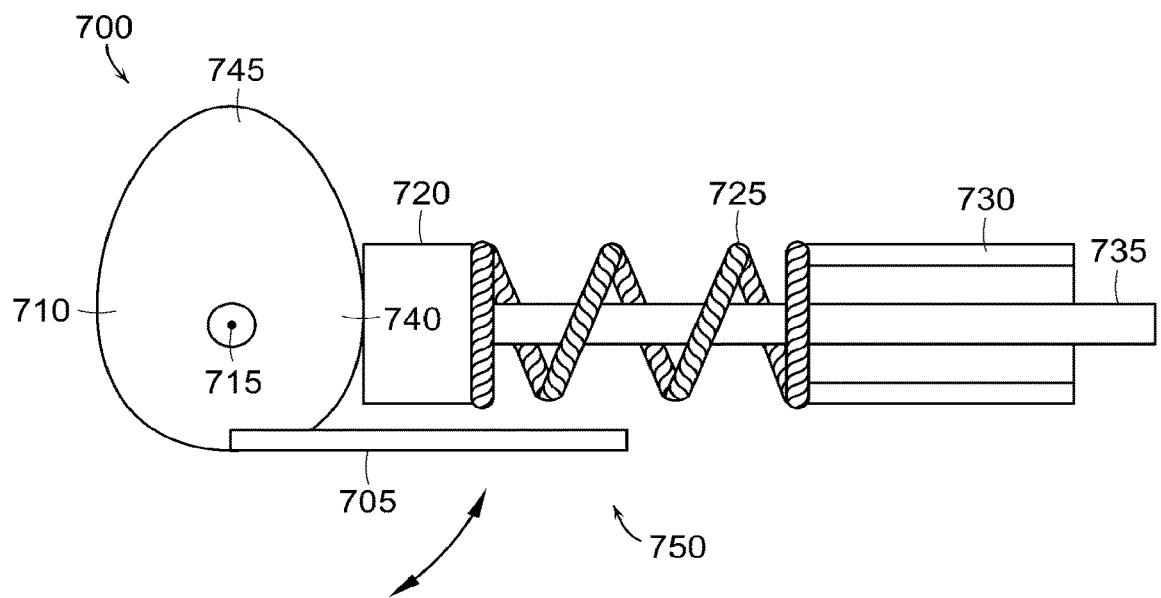
FIG. 7A is a schematic side view of a lever and cam sub assembly in a closed position, in accordance with one embodiment of the invention.
Figure 7B:
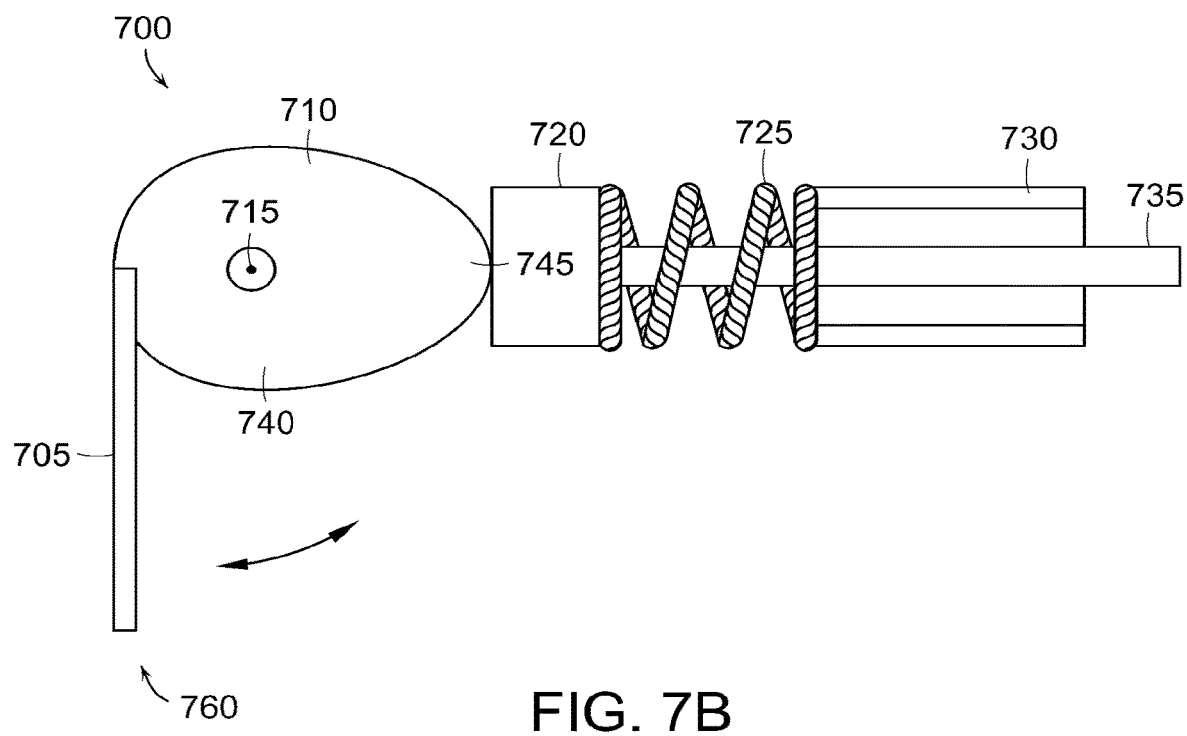
FIG. 7B is a schematic side view of the lever and cam sub assembly of FIG. 7A in an open position.

A simplified example lever and cam sub assembly 700 is shown in FIGS. 7A and 7B. In this embodiment, the lever 705 and cam 710 pivot about an axis 715. An anchoring element 720 is forced against the side of the cam 710 by a compression spring 725. A mounting element 730 holds the distal end of the compression spring 725 at a fixed position with respect to the cam axis 715. An elongate element 735 is anchored to the anchoring element 720 and extends through the center of the compression spring 725 and mounting element 730. In an alternative embodiment, the mounting element 730 may be moveable with respect to the cam axis 715, for example through a threaded screw arrangement.

In operation, when the lever 705 is in a closed position 750, as shown in FIG. 7A, the spring pushes the anchoring element 720 against the small radius side 740 of the cam 710, resulting in the anchoring element 720 providing a force holding the elongate element 735 in a first position close to the axis 715. When the lever 705 is moved to an open position 760, as shown in FIG. 7B, the large radius side 745 of the cam 710 pushes the anchoring element 720 away from the axis 715, resulting in the spring element 725 being compressed and foreshortened. As a result, the anchoring element 720 and elongate element 735 are held in a second position extending further away from the axis 715. It should be noted that the position of the lever is infinitely variable within its range of motion and can, in one embodiment, be held at any location by friction between the closed position and the open position, thus providing any intermediate position for the anchoring element 720 and the elongate element 735 and resultant intermediate force.

In one embodiment, the elongate element 735 is a band anchored at its distal end to a distal end of a slotted tube assembly for a curved drill and/or reamer device. In this embodiment, turning the lever 705 from a closed position 750 to an open position 760 will reduce the tension on the band and allow the distal end of the slotted tube assembly to be straightened more easily (i.e. without the need for a force sufficient to overcome the spring force provided by the compression spring 725). However, even when the lever 705 is in the closed position 750, by including the spring element 725, the distal end of the drill or reamer can still be straightened if it is subject to a force sufficient to overcome the spring force. As a result, the distal end of the drill or reamer is free to increase or decrease its curvature as required, if it abuts against a more solid object capable of overcoming the spring force on the distal end of the slotted tube assembly and deflecting the tip of the drill. In an alternative embodiment, the spring element 725 can be removed and the anchoring element 720 can be rotatably coupled directly to the cam 710.

In one embodiment, the anchoring element 720 can include, but is not limited to, at least one of a cam pusher assembly, a band retention element, a bushing, a flange, a handle portion, and/or any other appropriate anchoring element for a portion of a curved drilling and/or reaming device. In one embodiment, the mounting element 730 can include, but is not limited to, a feed screw, a bushing, a feed nut, a flange, a handle portion, or any other appropriate mounting element for a portion of a curved drilling and/or reaming device. The elongate element 735 can include a band, a wire, a shaft, a tube, a sheath, or any other appropriate elongate member for use in a curved drilling and/or reaming device.

In an alternative embodiment, the anchoring element 720, mounting element 730, and/or elongate element may be portions of a stent delivery device adapted to deploy a stent within a cavity created within a vertebral body, or be portions of any other appropriate devices used for the treatment of vertebral bodies or other bones.

In an alternative embodiment, the lever and cam sub assembly can be replaced by a screw assembly, a slider assembly, a trigger assembly, a rotating helix assembly, or any other appropriate assembly or mechanism for moving the anchoring element 720 with respect to the mounting element 730 to compress and foreshorten the spring element 725.

In one embodiment, the elongate element 735 can include an element providing a restoring force to straighten the distal end of a drill or reamer. This can allow the lever to provide a controllable curvature to the distal end of the drill or reamer, with the increase in angle through which the lever is turned corresponding to a decrease in the curvature of the distal end of the drill or reamer. Indicator markings on the handle of the drill can then be used to allow a user to set the distal end of the drill or reamer to any desired curvature by turning the lever to the desired location.

One embodiment of the invention includes a combined drilling and reaming assembly. An example combined drilling and reaming device 800 is shown in FIGS. 8A-8J. In this embodiment, the combined drilling and reaming device 800 is adapted to function as both a drill and a reamer. Integral systems are provided to deploy and retract a pivotable blade, to straighten and curve a slotted tube, and to constrain drilling and reaming operations The combined drilling and reaming device 800 can include a drive handle 805, a pivotable blade 810 attached to a flexible torque transmitting drive shaft 815 positioned within a slotted tube assembly 820, and a handle drive assembly 825 positioned within the handle 805. The slotted tube assembly 820 can be a spring loaded, flexible, slotted metal tube. A raised spline or key component 830 can be located on the slotted tube assembly 820 to ensure that, during operation, the combined drilling and reaming device 800 is inserted and locked into the working channel, such as a hollow cannula, in the desired circumferential orientation. A drill feed nut 835 including a locking flange 840 can be threaded onto the handle drive assembly 825 located within the handle 805. The locking flange 840 provides a locking feature for releasably locking the combined drilling and reaming device 800 to a cannula.

In one embodiment, the drive handle 805 includes two levers 845 on opposite sides of the drive handle 805. The levers 845 form part of a lever and cam sub-assembly to compress and foreshorten a compression spring 850 within the drive handle 805, thus allowing the distal end 855 of the slotted tube assembly 820 to flex back to a substantially straightened configuration. The levers 845 are pivotably connected to anchoring elements 860 such that, upon depression of the levers 845, the levers 845 drive a cam element 865 embedded within the drive handle 805 forward towards a distal end of the drive handle 805. The cam element 865 in turn compresses and foreshortens the compressed spring element 850 which is embedded within the drive handle 805 and connected to an elongate tensioning element (not shown) that extends along an interior of the slotted tube assembly 820 and provides a bending force to a distal end 855 thereof.

In operation, when the levers 845 are depressed, the cam element 865 is driven against the spring element 850, thereby compressing and foreshortening the spring element 850. As the spring element 850 is compressed, the force it applies to the elongate tensioning element is reduced, thereby reducing the bending force on the distal end 855 of the slotted tube assembly 820. The distal end 855 of the slotted tube assembly 820 is therefore allowed to return toward an unstressed, straight configuration. Similarly, releasing the levers 845 allows the spring element 850 to elongate, thereby reapplying a bending force to the distal end 855 of the slotted tube assembly 820 and returning the distal end 855 of the slotted tube assembly 820 to its spring-loaded, curved configuration.

In an alternative embodiment, the levers 845 may be replaced by alternative actuation elements such as, but not limited to, buttons, switches, threaded elements, electromagnetic elements, and/or sliding elements. In a further alternative embodiment, other mechanisms may be used to control the curvature of the distal end 855 of the slotted tube assembly 820 in addition to, or in place of, the lever and cam sub-assembly. These mechanisms include, but are not limited to, sliding elements, electromagnetic elements, ratcheting elements, and/or threaded elements. In one embodiment, the lever and cam sub-assembly, or alternative actuation mechanism, provide a binary control mechanism that, upon actuation, moves the distal end 855 of the slotted tube assembly 820 between two possible configurations, a straight and bent configuration. In an alternative embodiment, the lever and cam sub-assembly, or alternative actuation mechanism, can be infinitely variable within its range to allow the distal end 855 of the slotted tube assembly 820 to be fixed in any one of a plurality of configurations, ranging from straight to bent up to a predetermined maximum angle of curvature.

In an alternative embodiment, the drilling and reaming device 800 may be configured to create a straight cavity within a vertebral body. In this embodiment, the slotted tube assembly 820 is straight, and no lever and cam sub-assembly, or alternative actuation mechanism, is required for straightening and bending the distal end 855 of the slotted tube assembly 820.

The drive handle 805 also includes a rotatable knob 870 at a proximal end thereof. The rotatable knob 870 includes a locking element 875 that locks the rotatable knob 870 in position when not depressed (i.e. prevents rotation of the rotatable knob 870 relative to the drive handle 805), and which unlocks the rotatable knob 870 and allows it to rotate about a central elongate axis of the drive handle 805 when depressed. In alternative embodiments, alternative locking mechanisms including, but not limited to, buttons, sliding elements, hooks, threaded elements, pins, and/or electromagnetic elements may be used to lock and release the rotatable knob 870. In operation, depression of the locking element 875 by a user actuates a pin 880, sliding the pin out from one of a plurality of notches 885 and thereby freeing the rotatable knob 870 to rotate about the central elongate axis of the drive handle 805. A plurality of notches 885 may be placed within the handle 805 at various circumferential locations, thereby allowing the rotatable knob 870 to be rotated through, and locked at, a plurality of circumferential positions.

In operation, rotation of the rotatable knob 870 moves the pivotable blade 810 between a first, non-deployed, "drill" configuration (where an elongate axis of the pivotable blade 810 extends along the elongate axis of the tip of the slotted tube assembly 820) and at least one second, deployed, "ream" configuration (where the pivotable blade 810 is pivoted about a pivot point 812 at the end of the flexible torque transmitting drive shaft 815 such that the elongate axis of the pivotable blade 810 extends at an angle to the elongate axis of the tip of the slotted tube assembly 820). In one embodiment, the rotatable knob 870 is adapted to rotate between a first position, corresponding with an non-deployed blade 810 position, and at least one second position, corresponding to a deployed blade 810 position, with a greater angular rotation of the rotatable knob 870 corresponding to a greater angular pivoting of the pivotable blade 810.

For example, one embodiment of the invention includes a rotatable knob that can be rotated through, and locked at, three positions. Here, rotating the rotatable knob 870 through 90 degrees from its first, "drill," position pivots the pivotable blade 810 from the drill position to the a fully deployed ream position where the pivotable blade 810 is angled up to produce a maximum diameter of 10 mm (i.e., 5 mm radius "R" from the central elongate axis of the flexible torque transmitting drive shaft 815). Similarly, a half turn (45 degree) of the rotatable knob 870, positions the pivotable blade 810 to produce a maximum radial diameter of approximately 7 mm (i.e., 3.5 mm radius "R" from the central elongate axis of the flexible torque transmitting drive shaft 815). In the drill position, the pivotable blade 810 produces a void having a diameter of approximately 4 mm. In alternative embodiments, the pivotable blade 810 may be dimensioned and configured to pivot out to any appropriate radial distance from the central elongate axis of the flexible torque transmitting drive shaft 815 with "R" ranging between, for example, a minimum value (dependent upon the diameter of the blade 810, e.g., 2-6 mm, and more particularly, e.g., 4 mm) to 10 mm.

In one embodiment, the rotatable knob 870 may include a threaded, ratcheted, or otherwise controlled rotation mechanism, thereby allowing the rotatable knob 870 to be releasably held at a plurality of circumferential locations without the need for one or more pins 880 being releasably held by one or more notches 885. In this embodiment, the pivotable blade 810 may be set at any position between an non-deployed, "drill" configuration and a maximally deployed reaming configuration, thereby allowing the pivotable blade 810 to ream holes of any appropriate diameter within the vertebral body.

The rotatable knob 870 is connected to a dial tube 890 that is adapted to rotate within the drive handle 805. The dial tube includes a first set of angled slots 895 engaging a first set of pins 900, and a second set of angled slots 905 engaging a second set of pins 910. The second set of pins 910 also engage a slot 915 in the outer shell 920 of the drive handle 805. Each of the first set of pins 900 and the second set of pins 910 are anchored to a central torque driver 925.

The rotatable knob 870 at the proximal end of the drive handle 805 is indirectly connected to the drive mechanism via dial tube 890 and torque driver 925, and first set of pins 900 and the second set of pins 910. The dial tube 890 is a hollow cylindrical component which is free to rotate within the outer shell 920 of the drive handle 805. The dial tube 890 includes angled slots 895, 905 milled into its wall. The torque driver 925 is fixed to the rigid portion of a torque tube 930 by a set screw, and to the dial tube 890 via the second threaded pins 910 which mate and ride within the second angled slots 905. The torque driver 925 fits into the hollow core of the dial tube 890. When the rotatable knob 870 is turned, the dial tube 890 rotates and the torque tube 930 translates linearly along the elongate axis of the drive handle 805 resulting from a rotary to linear motion conversion due to the interaction of the pins 910 and the angles slot 905. As the rotatable knob 870 is turned to the "drill" position, the entire flexible shaft assembly 825 moves axially in the posterior direction (i.e. towards the proximal end of the drive handle 805), for example by approximately 2-3 mm, which in turn moves and retracts the pivotable blade 810 toward the distal end 855 of the slotted tube assembly 820.

A second actuation component in the dial tube 890 also moves linearly with rotatable knob 870 rotation via the first pins 900 and slot 895 in the dial tube 890. A tensioning component 935 is also housed in the dial tube 890. The tensioning component 935 is slidingly joined by set screws 940 to the torque driver 925. A double set screw cross pin assembly 945 nests within the tensioning component 935 and secures a blade actuation wire 950 running through the core of the device 800 to the pivotable blade 810. The blade actuation wire 950 may be constructed from a metal such as, but not limited to, nitinol, steel, aluminum, or combinations thereof. The wire 950 may, for example, be a shape set nitinol (nickel titanium) wire with a preformed curvature (i.e. formed with a curvature prior to assembly of the device) which is crimped at a distal end to the pivotable blade 810 and held at a proximal end to the tensioning pin assembly 945. The wire 950 elastically deforms (straightens) with tensioning, and returns to its preset shape when the tension is removed. Therefore, the pivotable blade 810 is capable of angling up and down with rotatable knob 870 actuation.

Figure 8A:
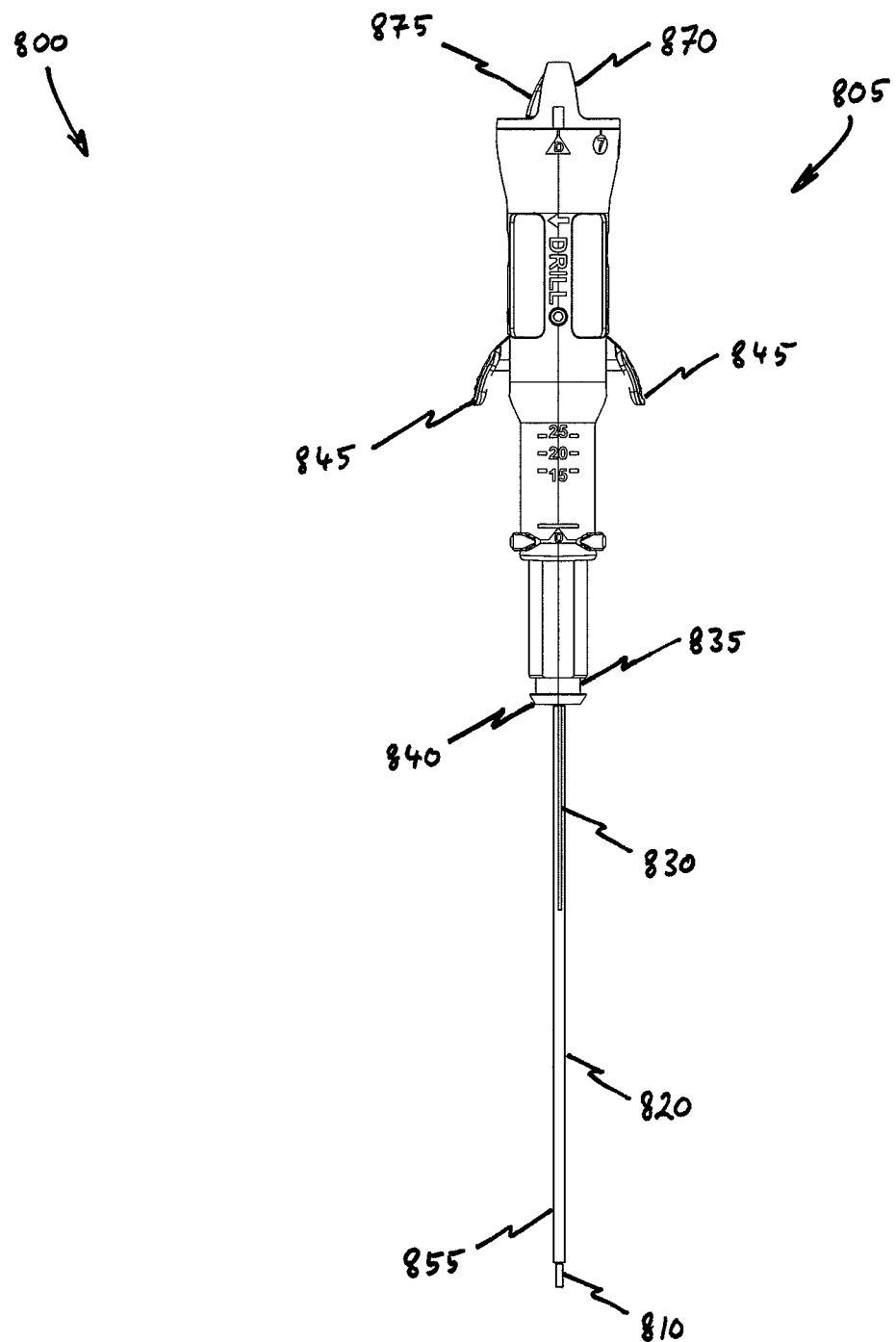
FIG. 8A is a front view of a combined drilling and reaming assembly, in accordance with one embodiment of the invention.
Figure 8B:
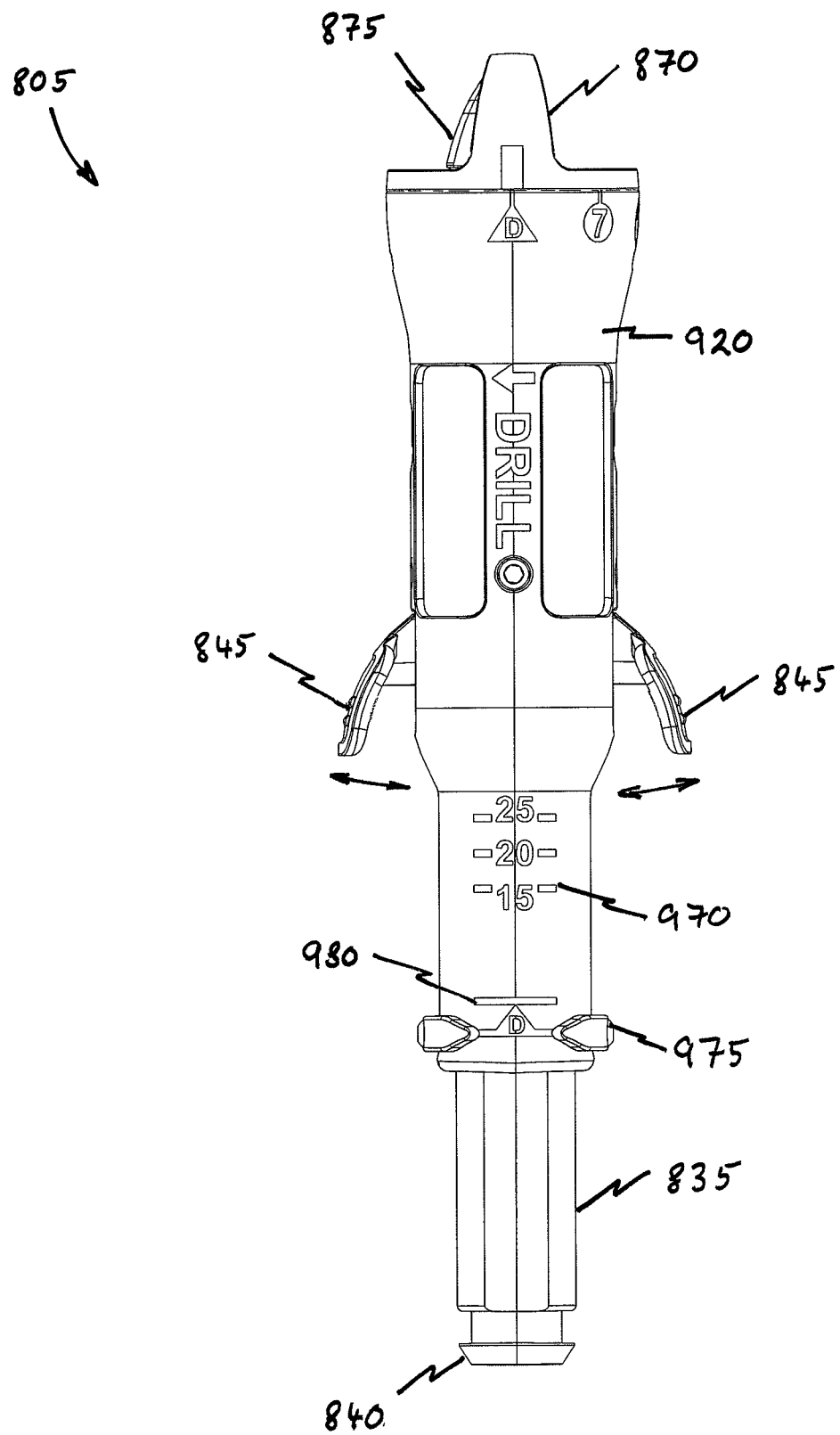
FIG. 8B is a front view of a drive handle for the combined drilling and reaming assembly of FIG. 8A.
Figure 8C:
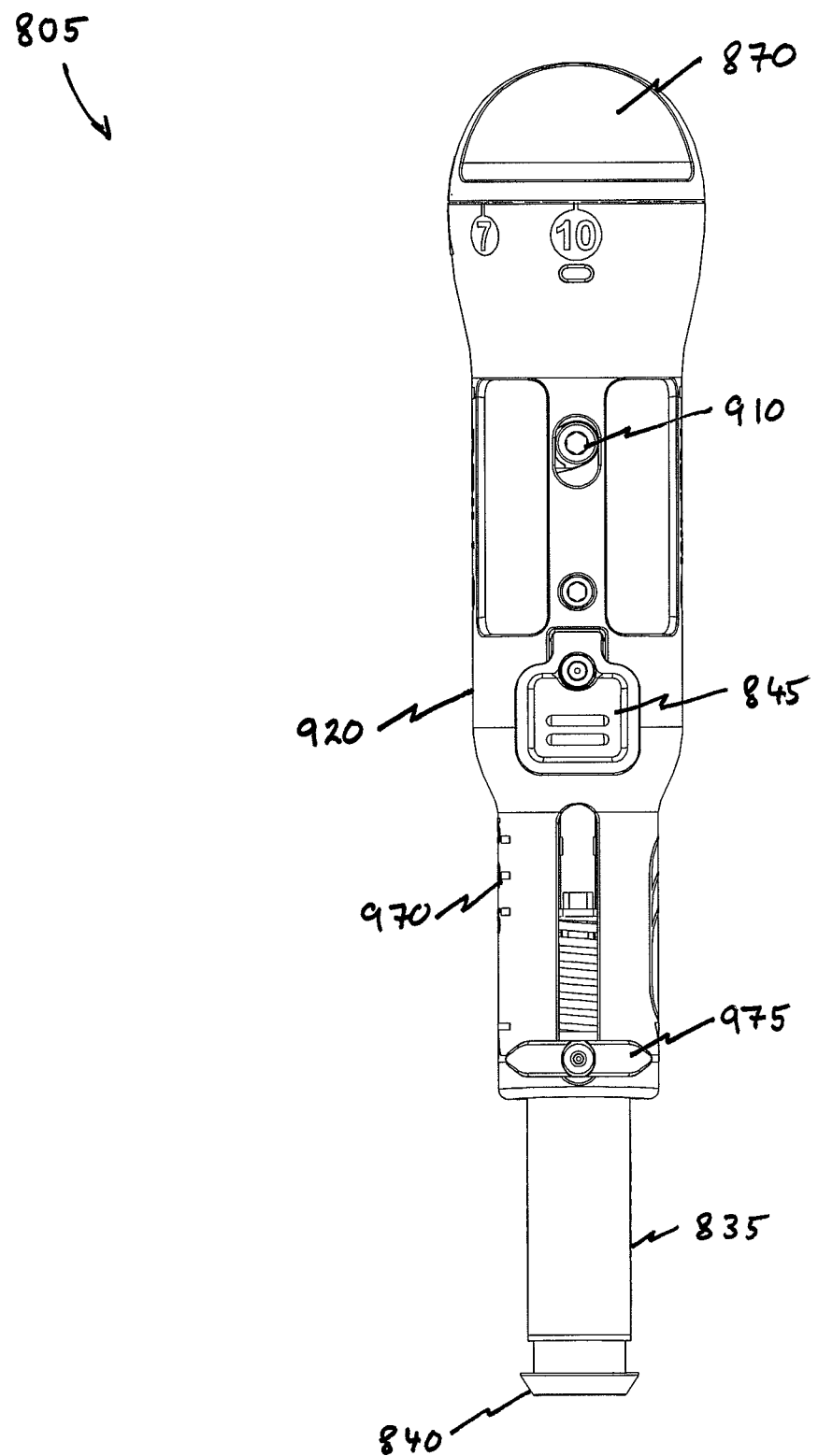
FIG. 8C is a side view of the drive handle for the drilling and reaming assembly of FIG. 8A.
Figure 8D:
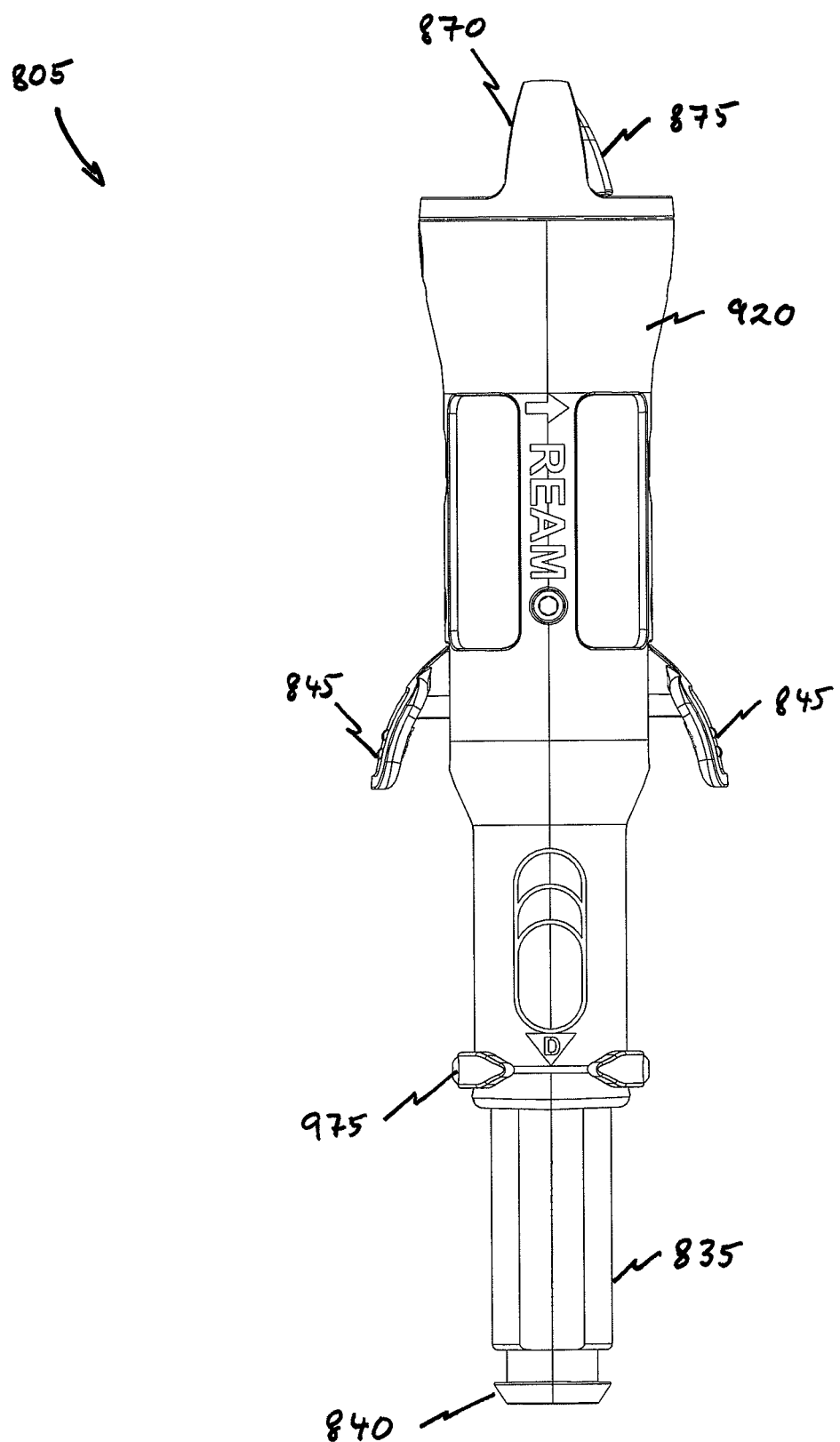
FIG. 8D is a rear view of the drive handle for the drilling and reaming assembly of FIG. 8A.
Figure 8E:
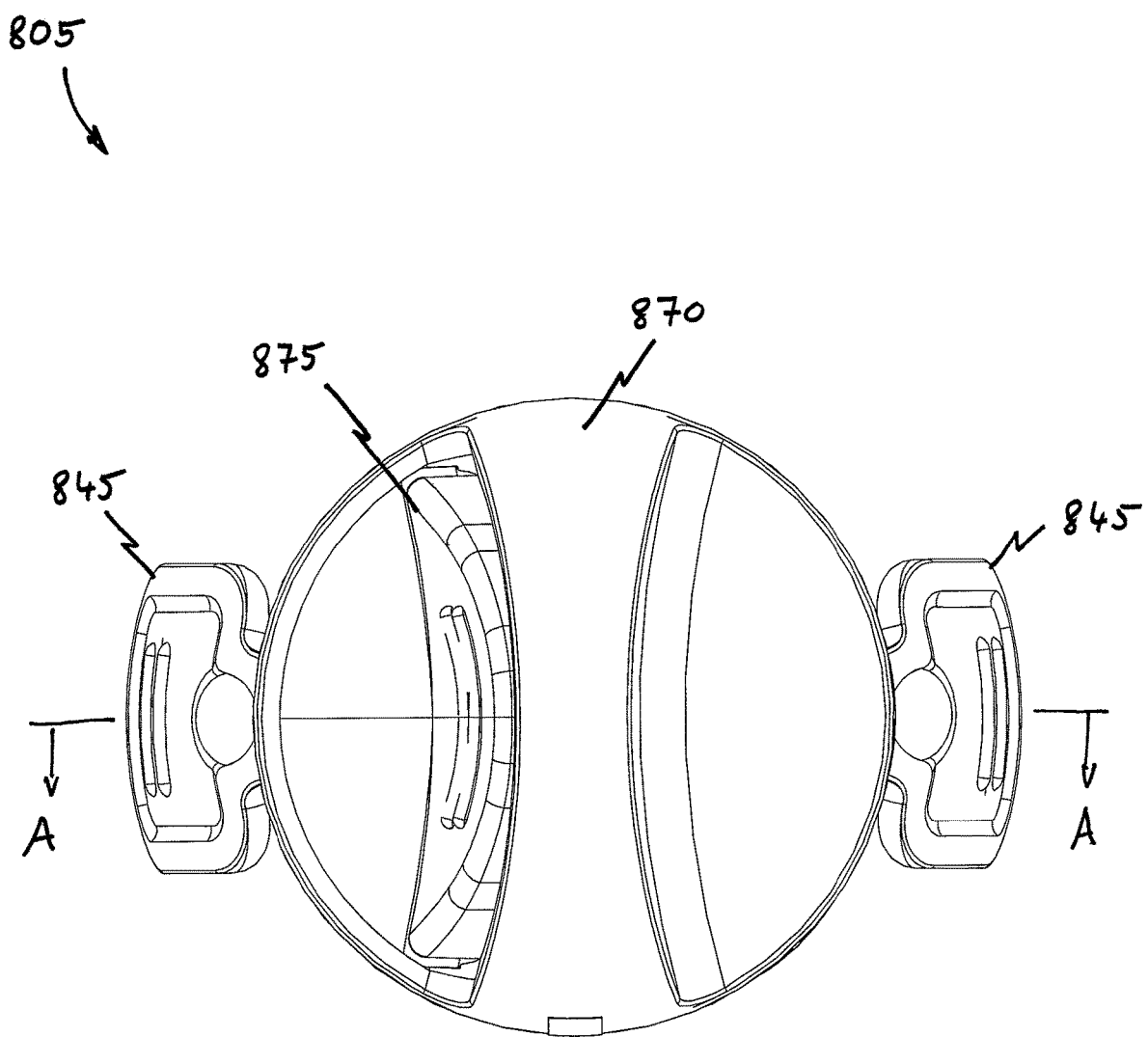
FIG. 8E is a top view of the drive handle for the drilling and reaming assembly of FIG. 8A.
Figure 8F:
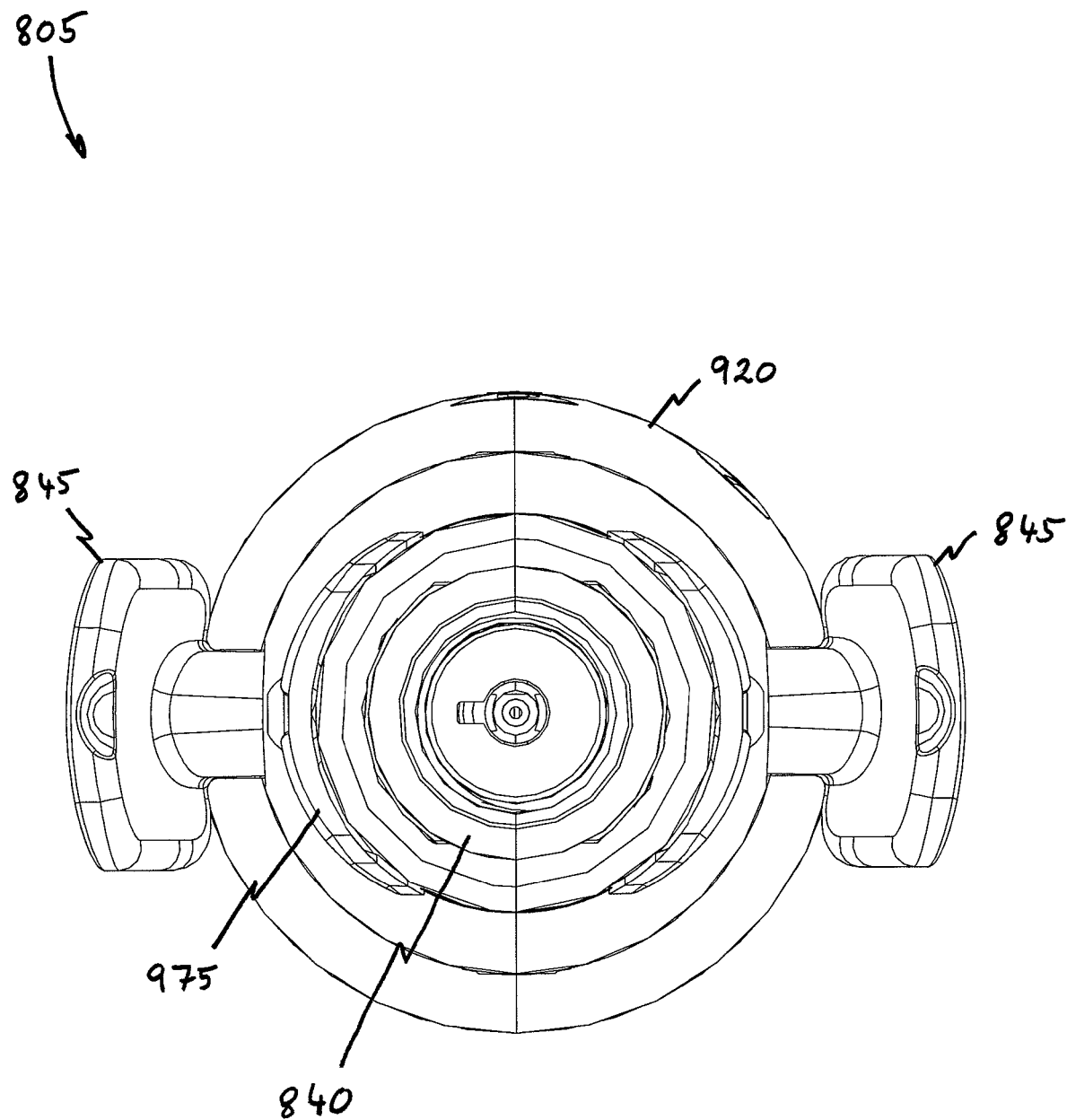
FIG. 8F is a bottom view of the drive handle for the drilling and reaming assembly of FIG. 8A.
Figure 8G:
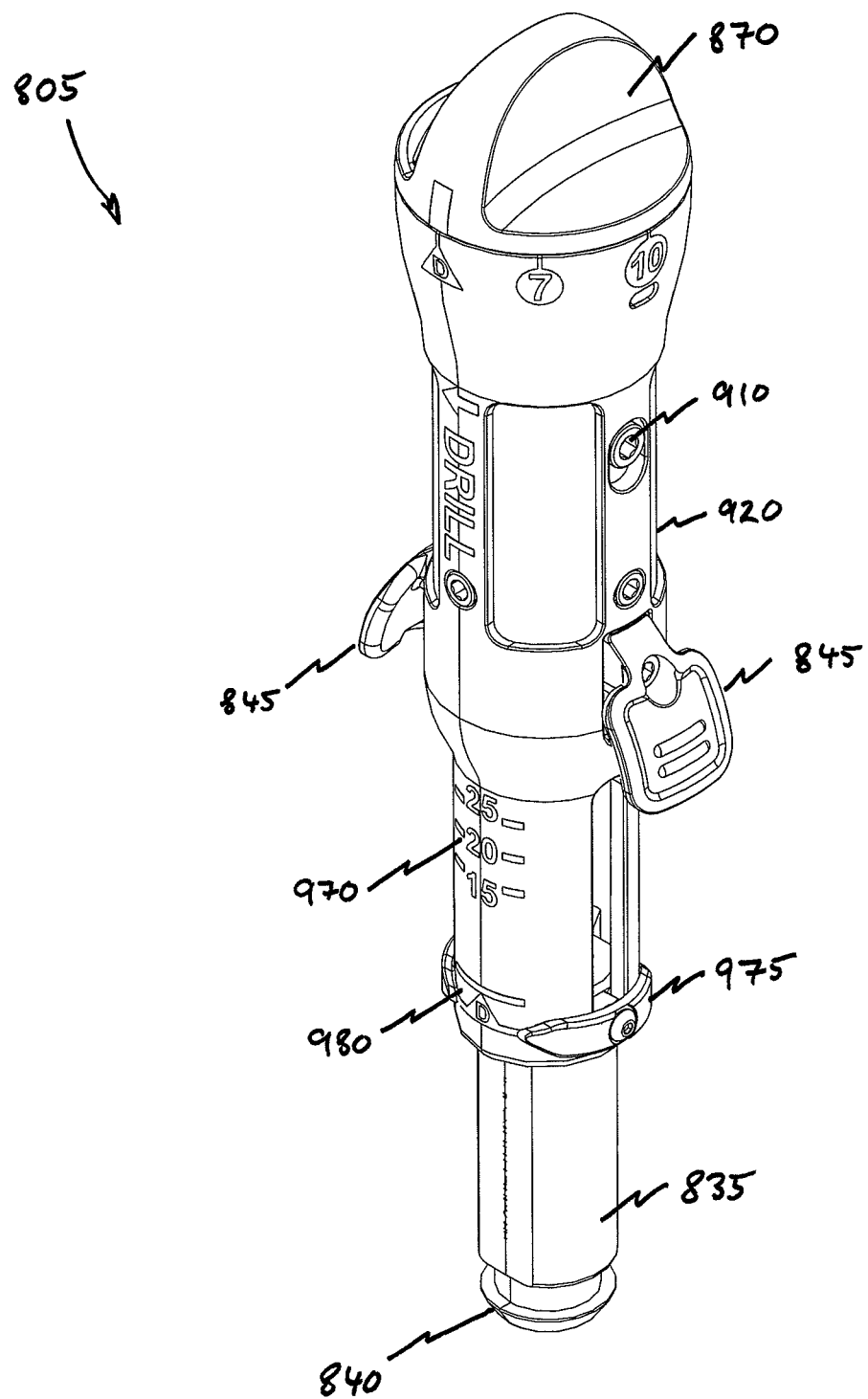
FIG. 8G is a perspective view of the drive handle for the drilling and reaming assembly of FIG. 8A.
Figure 8H:
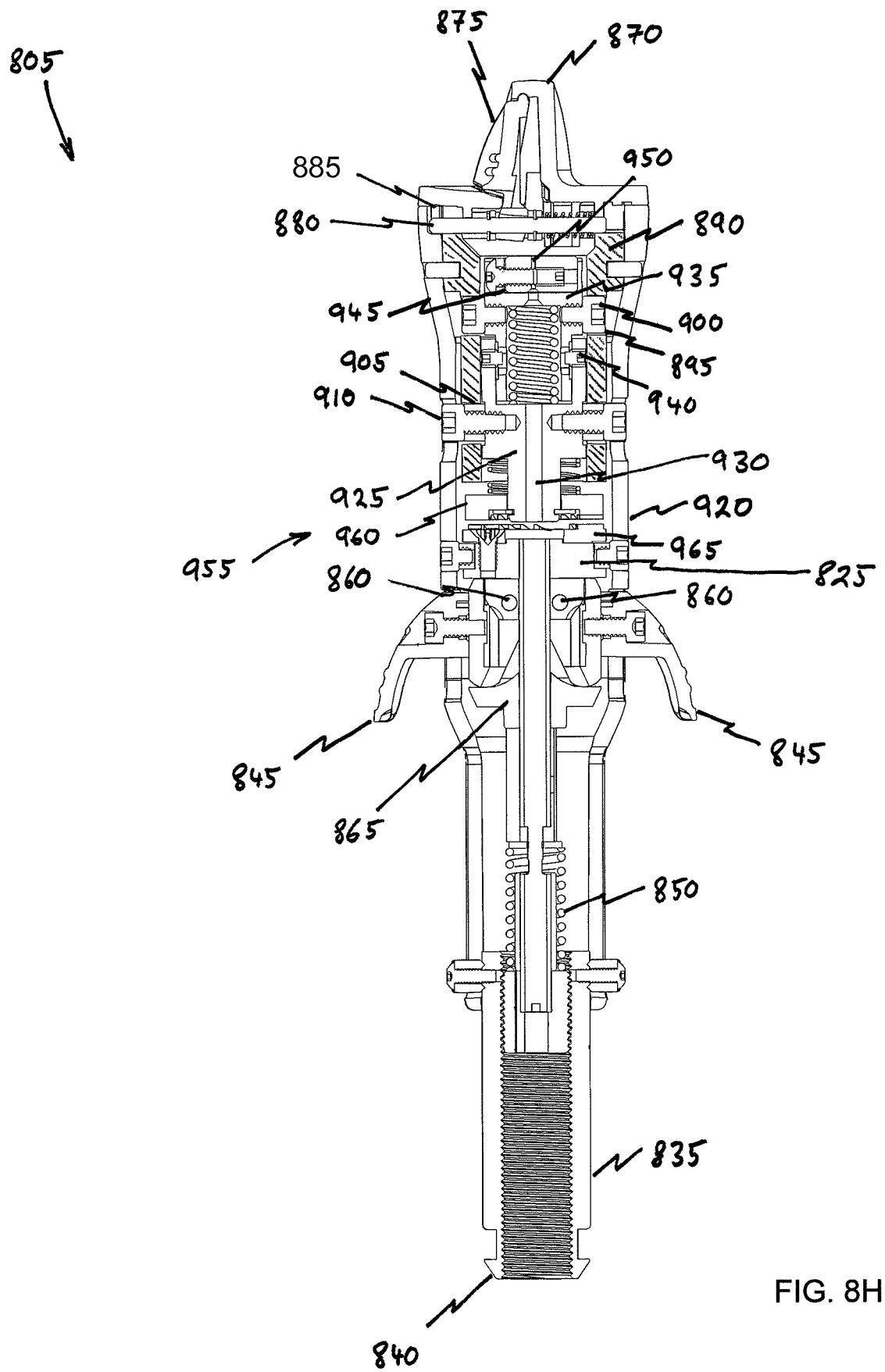
FIG. 8H is a sectional front view of the drive handle for the drilling and reaming assembly of FIG. 8A through section A-A.
Figure 8I:
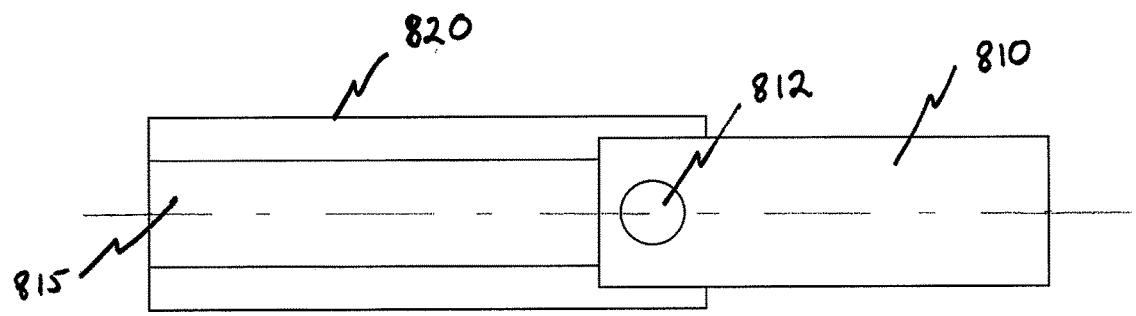
FIG. 8I is a schematic side view of a pivotable blade for the drilling and reaming assembly of FIG. 8A in an non-deployed, "drill" position.
Figure 8J:
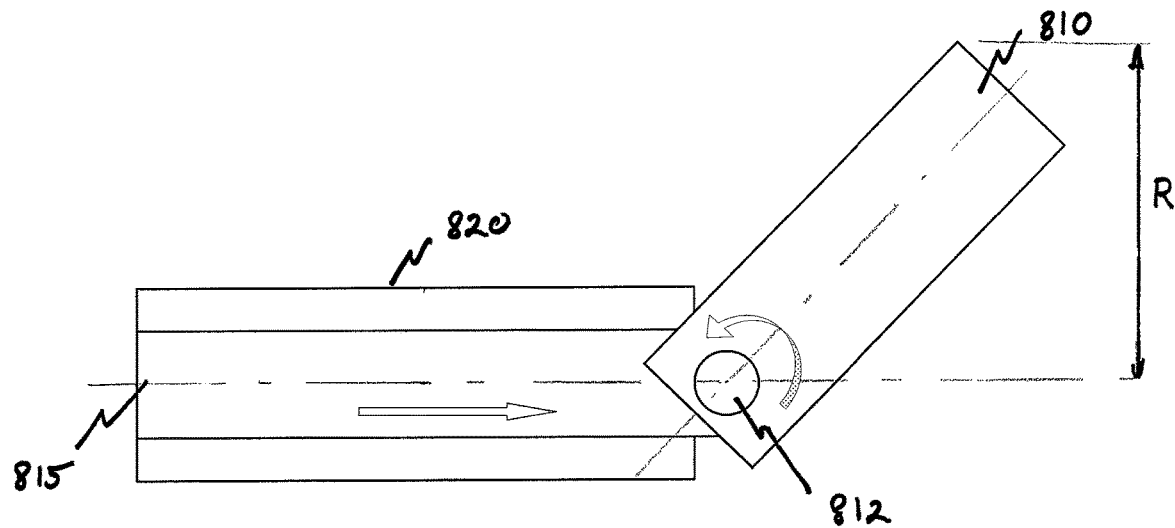
FIG. 8J is a schematic side view of a pivotable blade for the drilling and reaming assembly of FIG. 8A in a deployed, "ream" position.

By coupling the axial movement of the torque tube 930 with the blade wire tensioning, the pivotable blade 810 is retracted into a partially countersunk position within the slotted tube assembly 820 when being held in an non-deployed "drill" position. More particularly, due to a difference in the circumferential angle of the first slot 895 and second slot 905, the pins 900, 910 joined to the torque driver 925 and tensioning component 935 are moved apart (along the elongate axis of the assembly) with rotatable knob 870 rotation (from a "drill" position to a "ream" position), and therefore the tensioning component 935 and torque driver 925 separate. The rotatable knob 870 rotation simultaneously moves the tensioning component 935 more proximally (i.e. towards a proximal end of the drive handle 805) to tension the wire 950 and pivot the pivotable blade 810 out from the central elongate axis of the assembly, and moves the torque driver 925 more distally (i.e. towards a distal end of the drive handle 805) to force the torque tube 930 to move distally. These combined motions raise the pivotable blade 810 to the ream position. An example pivotable blade 810 position for a drill configuration is shown in FIG. 8I, with a corresponding example pivotable blade 810 position for a ream configuration shown in FIG. 8J. In an alternative embodiment, any appropriate means of pivoting the blade 810 from a drill to a ream configuration may be utilized instead of, or in addition to the dial tube 890 assembly. Such means may include, for example, threaded, slotted, levered, and/or electromagnetic mechanisms.

In addition, a ratchet mechanism 955 is linked to the rotatable knob 870 rotation and engages and disengages based on the position of the rotatable knob 870. More particularly, the ratchet mechanism 955 engages when the rotatable knob 870 is rotated to a "ream" position, thereby allowing the pivotable blade 810 to only be translated proximally (i.e. back towards the handle 805) when reaming. The ratchet mechanism 955 disengages when the rotatable knob 870 is rotated to a "drill" position, thereby allowing the pivotable blade 810 to be translated both proximally (i.e. back towards the handle 805) and distally (i.e. away from the handle 805) when drilling. In one embodiment, the blade 810 is translated distally by a clockwise rotation of the drive handle 805, and translated proximally by a counter-clockwise rotation of the drive handle 805. In another embodiment, the rotations may be reversed. The ratchet mechanism 955 includes a mobile, spring loaded ratchet component 960 connected to the torque driver 925 (and moving linearly along the elongate axis of the assembly with the torque driver 925) and a fixed ratchet component 965 connected to the handle drive assembly 825.

When the drive handle 805 is inserted into a cannula and locked in place, the drive handle 805 is free to be rotated about its central elongate axis. A rotation of the drive handle 805 in one direction (for example a clockwise rotation) rotates the flexible torque transmitting drive shaft 815 and pivotable blade 810 while simultaneously translating the blade 810 distal away from the drive handle 810 and out of the distal end 855 of the slotted tube assembly 820. A rotation of the drive handle 805 in an opposite direction (for example a counter-clockwise rotation) rotates the flexible torque transmitting drive shaft 815 and pivotable blade 810 while simultaneously translating the blade 810 proximately towards the drive handle 805 and back into the distal end 855 of the slotted tube assembly 820. When in a drill configuration (i.e. with the blade 810 retracted and parallel with the elongate axis of the tip of the slotted tube assembly 820), the pivotable blade 810 is free to rotate and translate in both directions, subject to the internal threading in the drill feed nut 835. As a result, the device 800 can act as a simple curvilinear drilling device in procedures where no reaming is required. However, in a ream configuration (i.e. with the blade 810 pivoted away from the elongate axis of the tip of the slotted tube assembly 820), the ratchet mechanism 955 is engaged and the blade can only translate proximally towards the drive handle 805 while being rotated. In an alternative embodiment, the ratchet mechanism 955 may not be used (or may be engagable and disengageable through a separate ratchet mechanism 955 actuator), and the blade may therefore be capable of being translated both proximally and distally when in both the drill and ream configurations.

In one embodiment, a scale 970 may be placed on the outer shell 920 of the drive handle 805 (or, in alternative embodiments, at any other appropriate location) to indicate the distance by which the blade 810 has been translated out from the distal end 855 of the slotted tube assembly 820. An indicator element 975 coupled to the drill feed nut 835 (or, in alternative embodiments, to another appropriate location) may slide along the scale 970 as the blade 810 is rotated and translated, to indicate how far the blade 810 has extended from the distal end 855 of the slotted tube assembly 820. In the embodiment of FIGS. 8A-8J, the scale 970 indicates when the blade 810 is at the zero location 980 (i.e. at the distal end 855 of the slotted tube assembly 820) up to a distance of 25 mm from the distal end 855 of the slotted tube assembly 820. In alternative embodiments, any appropriate scaling may be used. In operation, the scale 970 indicates to a surgeon the drilling depth and reaming distance of the blade 810, thereby indicating the length of any cavity created by the blade 810.

In operation, the distal end of the combined drilling and reaming device 800 is inserted through a working channel of a cannula, in the drill configuration, and into an interior of a vertebral body while the levers 845 are depressed to straighten out the preformed curvature at the distal end 855 of the slotted tube assembly 820 and ease the passage of the slotted tube assembly 820 through the cannula. Upon insertion, the levers 845 are released, thereby allowing the distal end 855 of the slotted tube assembly 820 to take its preformed, curved shape as it exits the distal end of the cannula. The key component 830 is fed through the corresponding slot in the cannula to ensure correct orientation of the combined drilling and reaming device 800. The locking flange 840 is releasably locked into the cannula, thereby holding the device 800 longitudinally in place during operation.

Upon being positioned within, and releasably locked into, the cannula, the drive handle 805 is rotated in one direction (e.g. clockwise) to simultaneously rotate and distally translate the blade 810, thereby creating a drilled curvilinear hole in the vertebral body. Upon reaching the required distance into the vertebral body, as indicated by the scale 970 and indicator element 975, the locking element 875 is depressed and the rotatable knob 870 rotated, thereby pivoting the blade 810 into the ream configuration and engaging the ratchet mechanism 955. The specific ream configuration (i.e. the radial distance "R" of the tip of the blade from the central elongate axis) is set based on the rotation of the rotatable knob 870 relative to the handle 805. The drive handle 805 is then rotated in the opposite direction (e.g. counter-clockwise) to simultaneously rotate and proximally translate the blade 810 while in a ream configuration to ream out a larger cavity around the drilled hole.

Once the scale 970 and indicator element 975 indicates that the blade 810 has reamed back to the initial location, or any required location along the length of the drilled hole, the rotatable knob 870 is rotated back to its "drill" position to pivot the blade 810 back down to its non-deployed orientation. The blade 810 and slotted tube assembly 820 can then be removed from the cannula by disengaging the cannula's locking mechanism, depressing the levers 845, and pulling the assembly out of the cannula, thereby leaving a reamed cavity, such as a curvilinear cavity, in the vertebral body. This cavity can then be filled with stabilizing devices and/or materials to support and treat the damaged vertebral body. By providing a combined drilling and reaming device 800, the process of creating a cavity of a set size and shape within a vertebral body, or other targeted location within a patient, can be achieved without having to insert separate drilling tools and cavity enlarging tools into the body, thereby simplifying the surgical process and reducing the risk to the patient associated with the introduction of multiple devices in series. In various embodiments of the invention, the combined drilling and reaming device allows a pivotable blade to be inserted through a working channel and into a vertebral body, drill a hole, such as a straight or curvilinear hole, into the vertebral body with the blade in a first, non-deployed orientation, deploy the blade to a second, pivoted orientation, and ream out an enlarged cavity along the length, or a portion thereof, of the initially drilled hole, in a single procedure. Such combined drilling and reaming assemblies can include any appropriate combination of the components and mechanisms described herein.

In one embodiment, the combined drilling and reaming devices described herein are used in a posterior percutaneous surgical procedure by a unilateral approach. Dependent on the anatomy of the patient's vertebral body, either a transpedicular or extrapedicular approach may be used. In one embodiment, bi-planar imaging may be used to assist in the procedure. An example process for creating a cavity within a vertebral body for a posterior percutaneous surgical procedure is given below:

Example Combined Drilling/Reaming Procedure

Step 1: Site Location

Determine the correct surgical site by identifying the fractured vertebra with the use of intra-operative imaging in correlation with preoperative imaging studies. Proper positioning with pads or other table assisted support mechanisms may, in one embodiment, increase the potential for postural reduction of the vertebral body.

Step 2: Initial Procedural Access a. Using a dual C-arm technique, or other appropriate technique, place a biopsy needle (such as an 11 gauge biopsy needle) into the vertebral body following a lateral to medial placement while centering the needle parallel to and between the vertebral body endplates. After needle placement, remove the stylet and replace with a K-wire. Remove biopsy needle.

b. Place a cannula working channel over the K-wire, for example using directional markers on the device for proper medial orientation. Using lateral fluoroscopic guidance, or other appropriate guidance mechanisms, tap the working channel with a surgical mallet until the distal tip of the cannula portion of the working channel is anchored within the vertebral body to an appropriate depth (e.g., approximately 3-10 mm beyond the posterior wall). This depth is dependent upon the anatomy of the vertebral body being treated. Remove the K-wire.

c. Check medial arrow on the working channel to ensure it is oriented toward the patient sagittal midline. Remove trocar, leaving the working channel in place.

d. Once the working channel is at the desired depth, ensure established depth and orientation of the working channel is maintained at all times during the procedure. Particular vigilance should be exercised when inserting, locking, or removing components.

Step 3: Create Cavity a. Check combined drilling and reaming device markings of drive handle to confirm that the slide indicator and top cap are in the start position (i.e. blade in non-deployed "drill" configuration and retracted into distal end of slotted tube assembly).

b. Insert slotted tube assembly of combined drilling and reaming device into the working channel.

c. Disengage tension on curvature of distal end of tube assembly by squeezing levers on side of drive handle, thereby straightening the distal end.

d. Insert slotted tube assembly into the working channel, making sure to align the key with the slot, and continue advancing until locking flange locks into working channel. Release levers.

Note that the position of the path and cavity created by the combined drilling and reaming device may be adjusted by rotating the working channel prior to initiating combined drilling and reaming function. For proper cavity positioning, the degree of rotation will vary with working channel depth, anatomy and angle of access.

e. Secure working channel with one hand and rotate drive handle clockwise with opposite hand to advance blade (while in "drill" configuration).

f. Final position should be determined, for example, by distal blade tip proximity to medial portion of contralateral pedicle, and proximity to anterior vertebral body wall on lateral view. When nearing one of these two landmarks stop at the appropriate distance (e.g. 15 mm, 20 mm, or 25 mm) as listed on the numerical scale on the side of the drive handle.

g. Once desired depth position is achieved, unlock and rotate rotatable knob at proximal end of drive handle to the desired cavity diameter (e.g. 7 mm or 10 mm). This will pivot the blade to the required deployed configuration for reaming.

h. To create the cavity, secure the working channel with one hand and rotate the drive counterclockwise. In one embodiment, an audible clicking sound, due to the ratchet mechanism, may be heard.

i. Confirm with fluoroscopic imaging that the pivotable blade is deployed during rotation.

j. Cavity will be created as the deployed blade rotates and translated proximally back toward the distal end of the slotted tube assembly.

k. Cavity creation is complete when the slide indicator on the drive handle reaches the location marking the "zero" position.

l. Unlock and rotate rotatable knob back to "drill" position.

m. Continue counterclockwise rotation of the combined drilling and reaming handle to retract the blade into the slotted tube assembly.

n. Remove device from working channel by depressing release mechanism on the working channel with one hand while squeezing the levers on the side of the drive handle and pulling the slotted tube assembly and blade out of the working channel.

In alternative embodiments of the invention, any appropriate material, or combination of materials, may be used for the components described herein. Appropriate materials include, but are not limited to, stainless steel, aluminum, plastics, textiles, composite materials, or any combination thereof. The method of creating a cavity may include all, or only some of, the components described herein, depending upon the specific requirements of the system.

In further alternative embodiments of the invention, different drill and/or reamer devices can be used to create the cavity. These may include one or more blades or drill bits, looped or otherwise configured wires, or other drilling, boring, or reaming devices. The blades may be of any appropriate shape and configuration.

In one embodiment of the invention, a fiber optic camera device may be inserted into the cannula to provide images of the curvilinear pathway and cavity to a physician at any point during the procedure. The camera may also provide diagnostic information that may be used when determining the required size and shape of the cavity being created.

In alternative embodiments of the invention, the arc of the drilling device and/or reamer device may be selected to provide any shape of curvilinear cavity. Different arcs may be provided by selection of different tools, with each tool being set to provide one specific arc. Alternatively an individual device may be adaptably configured to provide an arc of any required curvature. In further alternative embodiments, drill and/or reamer devices can be used to create cavities within other bones of a body or within any other structural element, such as, but not limited to, spinal disc tissue. As a result, the methods and apparatus described herein can be used in the treatment of other bones within a body, such as, but not limited to, broken or otherwise damaged limb bones, or for disc fusion techniques.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A method of forming a void in bony structure, the method comprising the steps of:
    accessing a bony structure with a cannula;
    inserting a distal end of a combined drill and reaming device through the cannula and into the bony structure;
    manipulating the distal end of the combined drill and reaming device to create a void in the bony structure; and
    removing the distal end of the combined drill and reaming device from the cannula,
    wherein the drill and reaming device includes a handle; and
    a flexible drill shaft assembly extending from a distal end of the handle, comprising:
        a pivotable blade located at a distal end of the flexible drill shaft assembly, wherein the pivotable blade is configured to cut in both a non-deployed and deployed position;
        a flexible rotatable drive shaft coupled to the pivotable blade; and a flexible, moveable and non-rotatable housing,
        wherein the combined drill and reaming device includes a ratchet mechanism when engaged to a rotatable knob allows the pivotable blade to only be translated proximally and when disengaged from the rotatable knob allows the pivotable blade to be translated proximally and distally.

2. The method of claim 1, wherein the void formed comprises a curvilinear void.

3. The method of claim 2, wherein the step of manipulating of the distal end of the combined drill and reaming device comprises a simultaneous rotation and curvilinear translation of the pivotable blade.

4. The method of claim 2, wherein the step of manipulating of the distal end of the combined drill and reaming device comprises a simultaneous rotation and curvilinear translation of the pivotable blade away from a proximal end of the combined drill and reaming device while in a non-deployed configuration to drill a curvilinear void having a first effective cross-sectional diameter.

5. The method of claim 4, wherein the step of manipulating of the distal end of the combined drill and reaming device further comprises: pivoting the pivotable blade to a deployed configuration; and a simultaneous rotation and curvilinear translation of the deployed pivotable blade towards a proximal end of the combined drill and reaming device to ream a curvilinear void having a second enlarged effective cross-sectional diameter.

6. The method of claim 4, wherein the step of manipulating the distal end of the combined drill and reaming device comprises inducing a curvature in the distal end of the flexible drill shaft assembly.

7. The method of claim 1, wherein the flexible drill shaft assembly comprises a lever and cam sub assembly for varying a force used to apply a curvature to the distal end of the flexible drill shaft assembly.

8. The method of claim 1, further comprising the steps of: manipulating at least one lever to a first position to reduce a force on the distal end of the flexible drill shaft assembly prior to inserting the distal end of the drill device through the cannula; and releasing the at least one lever to a second position to increase the force on the distal end of the flexible drill shaft assembly after inserting the distal end of the drill device through the cannula.

9. The method of claim 8, wherein the distal end of the flexible drill shaft assembly comprises a predetermined curvature when the at least one lever is in a released configuration.

\* \* \* \* \*